United States Patent
Fik et al.

(10) Patent No.: US 10,548,817 B2
(45) Date of Patent: Feb. 4, 2020

(54) DENTAL ADHESIVE

(71) Applicant: DENTSPLY SIRONA Inc., York, PA (US)

(72) Inventors: Christoph P. Fik, Schonenberg (CH); Sven Pohle, Constance (DE); Joachim Klee, Radolfzell (DE)

(73) Assignee: DENTSPLY SIRONA INC., York, PA (US)

( * ) Notice: Subject to any disclaimer, the term of this patent is extended or adjusted under 35 U.S.C. 154(b) by 143 days.

(21) Appl. No.: 15/747,823

(22) PCT Filed: Jul. 27, 2016

(86) PCT No.: PCT/EP2016/067947
§ 371 (c)(1),
(2) Date: Jan. 26, 2018

(87) PCT Pub. No.: WO2017/017155
PCT Pub. Date: Feb. 2, 2017

(65) Prior Publication Data
US 2018/0221249 A1    Aug. 9, 2018

(30) Foreign Application Priority Data
Jul. 27, 2015  (EP) ..................................... 15178517

(51) Int. Cl.
*A61K 6/083* (2006.01)
*C08L 33/02* (2006.01)
*A61K 6/00* (2006.01)
*C08L 33/26* (2006.01)

(52) U.S. Cl.
CPC .......... *A61K 6/0023* (2013.01); *A61K 6/0017* (2013.01); *A61K 6/083* (2013.01); *C08L 33/02* (2013.01); *C08L 33/26* (2013.01)

(58) Field of Classification Search
None
See application file for complete search history.

(56) References Cited

U.S. PATENT DOCUMENTS

| | | | |
|---|---|---|---|
| 4,469,897 A | 9/1984 | Rivetti | |
| 5,320,886 A * | 6/1994 | Bowen | A61L 24/06 428/34.1 |
| 2006/0069181 A1 * | 3/2006 | Thalacker | A61K 6/0017 523/116 |
| 2007/0293642 A1 | 12/2007 | Klee | |
| 2009/0043008 A1 | 2/2009 | Klee | |
| 2010/0197824 A1 * | 8/2010 | Bissinger | A61K 6/0017 523/116 |
| 2011/0028589 A1 * | 2/2011 | Saimi | A61K 6/083 523/115 |
| 2013/0158157 A1 | 6/2013 | Stelzig | |
| 2018/0221249 A1 * | 8/2018 | Fik | A61K 6/0017 |

OTHER PUBLICATIONS

Polymer Composites, (Irini D. Sideridou, Laboratory of Organic Chemical Technology, Department of Chemistry, Aristotle University of Thessaloniki) p. 593-620. (Year: 2010)*
International Search Report dated Oct. 12, 2016.

* cited by examiner

*Primary Examiner* — Peter A Salamon
(74) *Attorney, Agent, or Firm* — Dentsply Sirona Inc.

(57) ABSTRACT

The present invention relates to an aqueous dental composition having a pH of less than 7 as well as to the use of a stabilizer for the preparation of an aqueous dental composition having a pH of less than 7. In particular, the present invention relates to an aqueous dental composition having a pH of less than 7 comprising (i) one or more polymerizable compounds having at least one polymerizable double bond; (ii) a polymerization initiator system containing a) an 1,2-diketone photoinitiator compound having a light absorption maximum in the range from 300 to 500 nm; and b) a coinitiator compound; (iii) a stabilizer of the following formula (I) and/or (II), wherein the Rs, which may be the same or different, independently represent a branched $C_{3-8}$ alkyl or alkenyl group, or a $C_{3-8}$ cycloalkyl or cycloalkenyl group, R' represents a hydrogen atom, a $C_{1-6}$ alkyl or $C_{2-6}$ alkenyl group, or a $C_{1-6}$ fluoroalkyl or $C_{2-6}$ fluoroalkenyl group, X represents a group selected from a $C_{1-8}$ alkyl group or a $C_{3-8}$ cycloalkyl group, and n is 0, 1 or 2; and a solvent mixture comprising an organic solvent and at least 1 percent by weight of water based on the total weight of the aqueous dental composition.

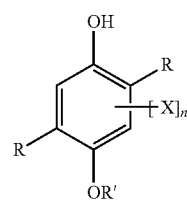

(I)

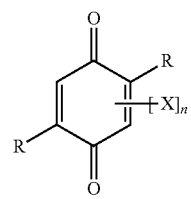

(II)

14 Claims, No Drawings

DENTAL ADHESIVE

FIELD OF THE INVENTION

The present invention relates to an aqueous dental composition having a pH of less than 7 as well as to the use of a stabilizer for the preparation of an aqueous dental composition having a pH of less than 7.

BACKGROUND OF THE INVENTION

Aqueous dental compositions having a pH of less than 7, i.e. acidic dental compositions, are known from the prior art. Such compositions are for example prepared in the form of universal etch or one-part self-etching, self-priming dental adhesive compositions which typically contain a mixture of polymerizable acidic compounds having at least one polymerizable double bond as well as an acidic group, further polymerizable compounds having at least one polymerizable double bond, and an initiator system in a suitable solvent.

The acidity of the mixture is adapted so that sufficient etching activity on dentin and enamel surfaces may be provided. However, a high acidity leads to complex stability problems due to the activation of chemical bonds of the functional components of the mixture. Specifically, ester bonds present in the polymerizable compounds may be solvolysed under acid catalysis. Moreover, the initiator system may be activated in the acidic medium leading to premature polymerization of the mixture.

As a result of the stability problems of such mixtures, the storage stability at room temperature of commercial one-part acidic dental compositions known from the prior art may be insufficient. Accordingly, conventional one-part acidic dental compositions must be stored under cooling in e.g. a refrigerator in order to avoid deterioration by solvolysis or polymerization.

EP-A 1 548 021 suggests one-part acidic dental compositions in the form of hydrolysis stable one-part self-etching, self-priming dental adhesive compositions containing specific monomers having improved resistance against hydrolysis under acidic conditions. In order to improve the stability of the composition, EP-A 1 548 021 suggests a stabilizer such as hydroquinone monomethylether, 2,6-di-tert.-butyl-p-cresol, tetramethyl piperidine N-oxyl radical and galvanoxyl radical.

EP-A 1 776 943 discloses one-part self-etching, self-priming dental adhesives having a pH of at most 2 which comprise an aqueous mixture containing a thermal polymerisation inhibitor in the form a 1,4-hydroquinone being substituted or unsubstituted at its benzene ring and optionally being etherified at one of its hydroxyl groups by means of a C1-C18 saturated hydrocarbon group. In particular, the specific inhibitors tert-butyl hydroquinone (TBHQ) and tert-butyl hydroxyanisol (BHA) are disclosed and tested in view of their ability to improve the stability of the dental adhesive composition compared with conventional inhibitors such as hydroquinone, hydroquinone monomethylether, bisphenol A and propyl gallate.

U.S. Pat. No. 5,320,886 A relates to a hydrophilic fluid crosslinking adhesive composition for dental application, which composition comprises hydrophilic monomers obtained as reaction products of a dianyhdride, a hydrophilic monomer and a reactive reagent. Furthermore, the composition may include water, a miscible volatile solvent, or a combination thereof. This document discloses long lists for each component of said adhesive composition, wherein among other inhibitors or stabilizers, 2,5-di-tertbutyl hydroquinone (DTBHQ) is listed. However, this document fails to disclose compositions having a pH of less than 7. Furthermore, the document is silent on stability problems upon storage. Rather, a stabilizer is primarily used during the synthesis of the hydrophilic monomers obtained from the starting materials dianyhdride, hydrophilic monomer and reactive reagent. For the purpose for use during this synthesis, 4-hydroxymethyl-2,6-di-tert-butylphenol and 2,6-di-tert-butyl-4-(dimethylamino) methyl-phenol are disclosed as particularly preferred stabilizers.

US 2006/0069181 A1 discloses a dental composition comprising 0.1 to 10 wt.-% of water, polymerizable compounds, a photoinitiator and a stabilizer. The stabilizer may be selected from a list including 2,5-di-tert-butyl hydroquinone.

US 2010/0197824 A1 discloses a non-aqueous dental compositions which may contain 2,5-di-tert-butyl hydroquinone as a stabilizer.

US 2011/0028589 A1 discloses a dental polymerizable composition in which at least a polymerizable monomer and a radical generator are contained in different parts of a two or three part composition. One part of the composition may comprise 2,5-di-tert-butyl hydroquinone as a polymerization inhibitor.

The present inventors found that acidic aqueous dental compositions known from the prior art are problematic in that the inhibitor used therein may give rise to discoloration problems upon storage and/or during photocuring under acidic conditions.

SUMMARY OF THE INVENTION

It is a problem of the present invention to provide an aqueous dental composition having a pH of less than 7 which does not give rise to discoloration upon storage and/or during photocuring and has a beneficial thermal stability upon storage.

It is a further problem of the present invention to provide a stabilizer for use in the preparation of an aqueous dental composition having a pH of less than 7, which stabilizer does not give rise to discoloration upon storage and/or during photocuring and has a beneficial thermal stability upon storage.

The present invention provides an aqueous dental composition having a pH of less than 7 comprising
(i) one or more polymerizable compounds having at least one polymerizable double bond;
(ii) a polymerization initiator system containing
  (a) an 1,2-diketone photoinitiator compound having a light absorption maximum in the range from 300 to 500 nm; and
  (b) a coinitiator compound;
(iii) a stabilizer of the following formula (I) and/or (II):

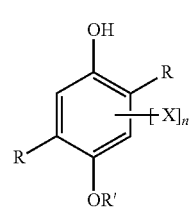

(I)

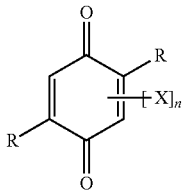

(II)

wherein
- the Rs, which may be the same or different, independently represent a branched $C_{3-8}$ alkyl or alkenyl group, or a $C_{3-8}$ cycloalkyl or cycloalkenyl group,
- R' represents a hydrogen atom, a $C_{1-6}$ alkyl or $C_{2-6}$ alkenyl group, or a $C_{1-6}$ fluoroalkyl or a $C_{2-6}$ fluoroalkenyl group,
- X represents a group selected from a $C_{1-8}$ alkyl group or a $C_{3-8}$ cycloalkyl group, and
- n is 0, 1 or 2; and (iv) a solvent mixture comprising an organic solvent and at least 1 percent by weight of water based on the total weight of the aqueous dental composition.

Furthermore, the present invention provides the use of a stabilizer of the following formula (I') or (II):

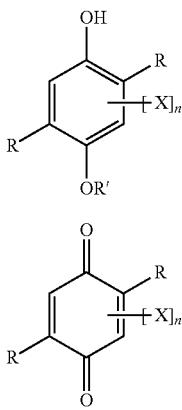

wherein
- the Rs, which may be the same or different, independently represent a branched $C_{3-8}$ alkyl or alkenyl group, or a $C_{3-8}$ cycloalkyl or cycloalkenyl group,
- R' represents a $C_{1-6}$ alkyl or $C_{2-6}$ alkenyl group, or a $C_{1-6}$ fluoroalkyl or $C_{2-6}$ fluoroalkenyl group,
- X represents a group selected from a $C_{1-8}$ alkyl group or a $C_{3-8}$ cycloalkyl group, and
- n is 0, 1 or 2, for the preparation of an aqueous dental composition having a pH of less than 7.

The present invention is based on the recognition that an aqueous dental composition having a pH of less than 7, which contains one or more polymerizable compounds having at least one polymerizable double bond, an 1,2-diketone polymerization initiator, coinitiator, a stabilizer and a solvent mixture comprising an organic solvent and water is particularly problematic with regard to discoloration. In particular, conventional stabilizers such as hydroquinone, hydroquinone monomethylether, 2,6-di-tert.-butyl-p-cresol, tetramethyl piperidine N-oxyl radical and galvanoxyl radical may impart stability to the dental composition, but give rise to discoloration problems.

The present invention is furthermore based on the recognition that a specific class of stabilizers avoids fully or at least substantially discoloration upon storage and/or during photocuring and a surprising stabilizing effect in an acidic aqueous mixture so that an aqueous dental composition having a pH of less than 7 may be provided which has no or substantially no discoloration upon storage and an excellent storage stability due to an improved resistance against premature polymerization.

DETAILED DESCRIPTION OF PREFERRED EMBODIMENTS

The term "aqueous dental composition" relates to a composition comprising a solvent mixture comprising an organic solvent and water in which water is preferably contained in an amount of at least 1 percent by weight based on the total weight of the aqueous dental composition. Commercially available organic solvents may contain a substantial amount of water. However, additional water is preferably added to the organic solvent.

The "pH of less than 7" of the aqueous dental composition according to the invention may be adjusted by any means known in the art, e.g. by adding predetermined amounts of one or more acidic compounds to the aqueous dental composition. In this context, the term "acidic compounds" denotes compounds having a $pK_a$ within the range of about −10 to 50. Examples of suitable inorganic acids are sulfuric acid, phosphonic acid, phosphoric acid, hydrochloric acid, nitric acid and the like, which may be used alone or in combination with each other. Examples of suitable organic acids are carboxylic acids which are preferably selected from the group consisting of formic acid, acetic acid, lactic acid, citric acid, itaconic acid, poly(meth)acrylic acid, itaconic acid, maleic acid, polyvinyl phosphonic acid, polyvinyl phosphoric acid, trifluoromethanesulfonic acid, toluenesulfonic acid, methanesulfonic acid, succinic acid, malic acid, tannic acid, toluene sulfonic acid, adipic acid, tartaric acid and ascorbic acid. The set pH-value of the aqueous dental composition may be stabilized by means of a typical chemical buffer system, that is a combination of a weak organic or inorganic acid having a $pK_a$ value at a temperature of 20° C. within the range of about 9 to 50 and its corresponding salt. Alternatively, the buffer system may be in the form of a Norman Goods buffer (Good's buffer) representing organic compounds having a $pK_a$ value at a temperature of 20° C. in a range between about 6 and 8, having biochemical inertness and being suitable for application in a biological system such as the human body. Examples for typical chemical buffer systems are acidic acid/acetate buffer, dihydrogenphosphate/monohydrogenphosphate buffer or a citric acid/citrate buffer. Examples for Good's buffers are 4-(2-hydroxyethyl)-1-piperazineethanesulfonic acid (HEPES), 2-(N-morpholino)ethanesulfonic acid (MES) or N-cyclohexyl-3-aminopropanesulfonic acid (CAPS). In connection with the term "pH-value" it is noted that the pH-value/system typically relates to aqueous systems wherein water is the main compound, i.e. present in an amount of about 90 percent by weight. In the present aqueous dental composition, water is typically not the main component. However, all pH-values indicated in the present application relate to pH-values determined by suitable standard means for determining the pH-value of aqueous systems, e.g. by means of a glass electrode.

Beside the aforementioned organic acids, any organic compounds comprising acidic functional groups may be applied for setting the pH of the present aqueous dental composition. For example, the polymerizable compound having at least one polymerizable double bond according to (i) may have at least one acidic functional group, or any further organic component(s) of the aqueous dental composition such as components of the polymerization initiator system according to (ii) or the organic solvent comprised in the solvent mixture according to (iv) may comprise acidic functional group(s).

The term "polymerization" relates to the combining by covalent bonding of a number of smaller molecules, such as monomers, to form larger molecules, that is, oligomers or polymers. The monomers may be combined to form only linear structures or they may be combined to form three-dimensional structures, commonly referred to as crosslinked polymers. In case of a higher conversion rate of the polymerizable compounds, the amount of multifunctional monomers may be reduced or the leaching problem may be alleviated.

The terms "curing" and "photocuring" mean the polymerization of functional oligomers and monomers, or even polymers, into a crosslinked polymer network. Curing is the polymerization of unsaturated monomers or oligomers in the presence of crosslinking agents.

The terms "photocurable" and "curable" refer to a dental composition that will polymerize into a crosslinked polymer network when irradiated for example with actinic radiation such as ultraviolet (UV), visible, or infrared radiation.

"Actinic radiation" is any electromagnetic radiation that is capable of producing photochemical action and can have a wavelength of at least 150 nm and up to and including 1250 nm, and typically at least 300 nm and up to and including 750 nm.

The term "polymerizable double bound" as used herein in connection with compound(s) according to (a) means any double bond capable of radical polymerization, preferably a carbon-carbon double bond. Examples of the polymerizable double bond include vinyl, conjugated vinyl, allyl, acryl, methacryl and styryl. More preferably, the polymerizable double bound is selected from the group consisting of acryl, methacryl, allyl and styryl. Acryl and methacryl may be (meth)acryloyl or (meth)acrylamide. Most preferably, for the compound(s) according to (a), the polymerizable double bound is acryl or methacryl.

The term "polymerization initiator system" refers to a system comprising an 1,2-diketone photoinitiator compound having a light absorption maximum in the range from 300 to 500 nm; and (b) a coinitiator compound. Optionally, the polymerization initiator system may further comprise a polymerization initiator auxiliary substance.

The term "1,2-diketone photoinitiator" denotes any chemical compound having 1,2-diketone functional group, which compound forms free radicals when activated, e. g. by exposure to light or interaction with a coinitiator and optionally a polymerization initiator auxiliary substance in a photochemical process.

The term "coinitiator" as used herein means an electron donor compound, i.e. a compound capable of donating electrons in a photochemical process. Suitable examples include organic compounds having heteroatoms with electron lone pairs, for example amine compounds.

The term "polymerization initiator auxiliary substance" refers to a molecule that produces an advantageous chemical change in any of the components of the polymerization initiator system in a photochemical process. For example, the polymerization initiator auxiliary substance may be selected from the group consisting of iodonium-, sulfonium- or phosphonium salts and aromatic tertiary phosphine compounds.

The term "one-part (composition)" as used herein means single-component dental compositions. Such compositions are typically packaged in only one container. Such compositions may be stored and allow application of the composition without any mixing and without any special equipment before the application.

The term "self-etching" means that the aqueous dental composition may be applied to a tooth without any preliminarily etching of enamel in a separate method step. Particularly, the pH of the present aqueous dental composition is set with the proviso that it allows the preparation of an aqueous dental composition which is hydrolysis stable preferably at 50° C. for at least 30 days, or at 60° C. or 70° C. for at least 3 days. Due to the high thermal stability of the composition of the present invention, dental composition having excellent shelf-life may be prepared.

The pH of the present aqueous dental composition is suitably set in view of the application, e.g. etching, but also in view of chemical compatibility with the further components comprised in the composition and/or in the restorative material. Preferably, the aqueous dental composition according to the present invention has a pH of less than 6.5, more preferably pH is from 1 to 6, even more preferably from 2 to 5.

The aqueous dental composition according to the present invention comprises a stabilizer of the formula (I) and/or (II). The aqueous dental composition according to the present invention may comprise one or more stabilizer(s) of the formula (I) and/or (II). Preferably, the stabilizer is a compound of formula (I) and/or (II) wherein Rs, which may be the same or different, independently represent a branched $C_{3-8}$ alkyl group or a $C_{3-8}$ cycloalkyl group, R' represents a hydrogen atom, a $C_{1-6}$ alkyl group or a $C_{1-6}$ fluoroalkyl group, and n is 0 or 1; more preferably, the stabilizer is a compound of formula (I) and/or (II) wherein Rs, which may be the same or different, independently represent a branched $C_{3-8}$ alkyl group, R' represents a hydrogen atom or a $C_{1-6}$ alkyl group, and n is 0; even more preferably, the stabilizer is a compound of the following formulae (Ia), (Ib) or (IIa):

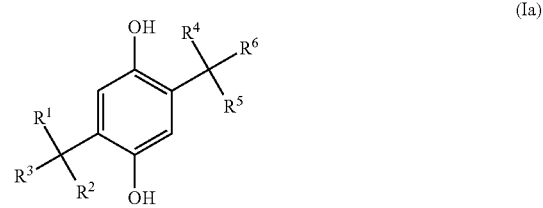

(Ia)

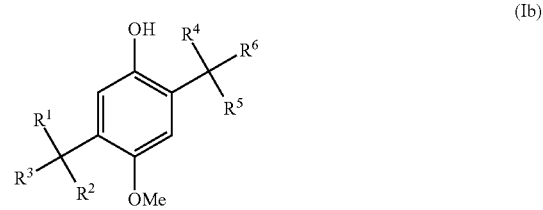

(Ib)

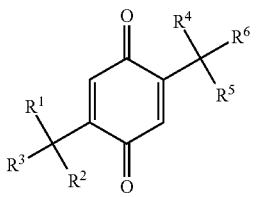

wherein the R¹, R², R³, R⁴, R⁵ and R⁶, which may be the same or different, independently represent a methyl or an ethyl group. It is particularly preferred that the stabilizer of formulae (Ia), (Ib) or (IIa) is a compound of the following formulae:

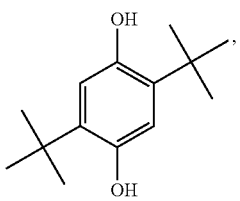

(DTBHQ)

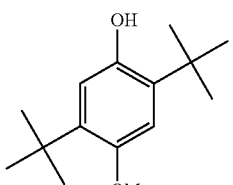

(DTBMP)

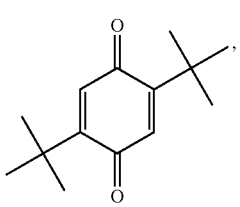

(DTBBQ)

preferably DTBHQ.

2,5-di-tert-butyl-hydroquinone (DTBHQ), 2,5-di-tert-butyl-4-methoxyphenol and 2,5-di-tert-butyl-benzoquinone (DTBBQ) are commercially available standard chemicals. In general, monoethers of formula (I) with R' being $C_{1-6}$ alkyl, a $C_{2-6}$ alkenyl group, a $C_{1-6}$ fluoroalkyl or $C_{2-6}$ fluoroalkenyl group, such as 2,5-di-tert-butyl-hydroquinone monoalkylethers of formula (Ib), may be readily obtained from a dihydroquinone of formula (I), such as DTBHQ, as starting material by means of selective monoetherification catalyzed in the presence of $NaNO_2$ in combination with an inorganic acid such $H_2SO_4$ or a solid acidic catalyst such as a styrene based sulfonated polymer, e.g. the commercially available ion exchange resins Amberlyst® 15 and Aberlite® IR120, analogously as described by C. Gambarotti et al. in *Current Organic Chemistry* 2013, 17, pages 1108 to 1113. Alternatively, monoethers of formula (I) with R' being $C_{1-6}$ alkyl, a $C_{2-6}$ alkenyl group, a $C_{1-6}$ fluoroalkyl or $C_{2-6}$ fluoroalkenyl group, such as 2,5-di-tert-butyl-hydroquinone monoalkylethers of formula (Ib), may be obtained by reacting a dihydroquinone of formula (I), such as DTBHQ, with an alkyl alcohol in the presence of a transition metal salt selected from copper and iron salts analogously as described in the U.S. Pat. No. 4,469,897.

The stabilizer DTBHQ is particularly preferred, since from the present experimental Examples it appears that this stabilizer provides the best results in view of the discoloration problematic, i.e. there is no or almost no discoloration of the aqueous dental composition upon storage at 50° C. for 30 days.

According to an alternative embodiment, compounds of formula (I) are preferred in which R' represents a $C_{1-6}$ alkyl or $C_{2-6}$ alkenyl group, or a $C_{1-6}$ fluoroalkyl or $C_{2-6}$ fluoroalkenyl group. More preferably, R' represents a $C_{1-6}$ alkyl group or a $C_{1-6}$ fluoroalkyl group, and most preferably, R' represents a $C_{1-6}$ alkyl group.

The aqueous dental composition according to the invention contains the stabilizer in an amount of 0.001 to 3 percent by weight, preferably 0.005 to 2 percent by weight, more preferably 0.01 to 1.2 percent by weight and even more preferably 0.05 to 1.0 percent by weight, yet even more preferably 0.075 to 0.9 percent by weight, and most preferably 0.1 to 0.8 percent by weight based on the total weight of the aqueous dental composition.

When the amount of the stabilizer (iii) is below the above indicated lower limit of 0.001, then storage stability of the aqueous dental composition might be insufficient, since the amount of stabilizer is too small to provide a stabilizing effect. However, when the amount of stabilizer (iii) is above the maximum threshold of 3 percent by weight, then the applicability of the aqueous dental composition might be negatively affected, since higher amounts of stabilizer may disturb or even substantially prevent intended polymerisation curing of the composition during application.

In order to provide an advantageous stability of the aqueous dental composition upon storage and/or during photo curing, to prevent or substantially prevent discoloration of said composition but also to provide a beneficial polymerization rate for photo curing, it may be preferred to set the molar ratio of (ii)(a) 1,2-diketone photoinitiator:(ii)(b) coinitiator compound: (iii) stabilizer(s) of formulae (I) and (II) within the range of 1:(0.3 to 3.0):(0.01 to 0.2), more preferably 1:(0.3 to 1.5):(0.01 to 0.1), even more preferably 1:(0.3 to 1.0):(0.01 to 0.05).

According to (i), the aqueous dental composition according to the present invention contains one or more polymerizable compounds having at least one polymerizable double bond.

Preferably, the one or more polymerizable compounds having a polymerizable double bond is/are selected from the group consisting of (meth)acrylate compound(s), N-substituted or N-unsubstituted alkyl acrylic or acrylic acid amide compound(s), mono-, bis- or poly(meth) acrylamides and bis(meth)acrylamide compounds. More preferably, the one or more polymerizable compounds having a polymerizable double bond includes a (meth)acrylamide, a (meth)acrylic acid ester and/or a bis(meth)acrylamide compound.

The (meth)acrylate compound may be selected from the group of methyl acrylate, methyl methacrylate, ethyl acrylate, ethyl methacrylate, propyl acrylate, propyl methacrylate, isopropyl acrylate, isopropyl methacrylate, 2-hydroxyethyl acrylate, 2-hydroxyethyl methacrylate (HEMA), hydroxypropyl acrylate, hydroxypropyl methacrylate, tetrahydrofurfuryl acrylate, tetrahydrofurfuryl methacrylate, glycidyl acrylate, glycidyl methacrylate, the diglycidyl methacrylate of bis-phenol A ("bis-GMA"), glycerol mono- and di-acrylate, glycerol mono- and dimethacrylate, ethyleneglycol diacrylate, ethyleneglycol dimethacrylate, polyethyleneglycol diacrylate (where the number of repeating ethylene oxide units vary from 2 to 30), polyethyleneglycol dimethacrylate (where the number of repeating ethylene oxide units vary from 2 to 30 especially triethylene glycol dimethacrylate (TEGDMA), neopentyl glycol diacrylate, neopentylglycol dimethacrylate, trimethylolpropane triacrylate, trimethylol propane trimethacrylate, mono-, di-, tri-, and tetra-acrylates and methacrylates of pentaerythritol (e.g. dipentaerythritol penta acrylate monophosphate (PENTA)) and dipentaerythritol, 1,3-butanediol diacrylate, 1,3-butanediol dimethacrylate, 1,4-butanedioldiacrylate, 1,4-butanediol dimethacrylate, 1,6-hexane diol diacrylate, 1,6-hexanediol dimethacrylate, di-2-methacryloyloxethyl hexamethylene dicarbamate, di-2-methacryloyloxyethyl trimethylhexanethylene dicarbamate, di-2-methacryloyl oxyethyl dimethylbenzene dicarbamate, methylene-bis-2-methacryloxyethyl-4-cyclohexyl carbamate, di-2-methacryloxyethyl-dimethylcyclohexane dicarbamate, methylene-bis-2-methacryloxyethyl-4-cyclohexyl carbamate, di-1-methyl-2-methacryloxyethyl-trimethyl-hexamethylene dicarbamate, di-1-methyl-2-methacryloxyethyl-dimethylbenzene dicarbamate, di-1-methyl-2-methacryloxyethyl-dimethylcyclohexane dicarbamate, methylene-bis-1-methyl-2-methacryloxyethyl-4-cyclohexyl carbamate, di-1-chloromethyl-2-methacryloxyethyl-hexamethylene dicarbamate, di-1-chloromethyl-2-methacryloxyethyl-trimethylhexamethylene dicarbamate, di-1-chloromethyl-2-methacryloxyethyl-dimethylbenzene dicarbamate, di-1-chloromethyl-2-methacryloxyethyl-dimethylcyclohexane dicarbamate, methylene-bis-2-methacryloxyethyl-4-cyclohexyl carbamate, di-1-methyl-2-methacryloxyethyl-hexamethylene dicarbamate, di-1-methyl-2-methacryloxyethyl-trimethylhexamethylene dicarbamate, di-1-methyl-2-methacryloxyethyl-dimethylbenzene dicarbamate, di-1-methyl-2-metha-cryloxyethyl-dimethylcyclohexane dicarbamate, methylene-bis-1-methyl-2-methacryloxyethyl-4-cyclohexyl carbamate, di-1-chloromethyl-2-methacryloxyethyl-hexamethylene dicarbamate, di-1-chloromethyl-2-methacryloxyethyl-trimethylhexamethylene dicarbamate, di-1-chloromethyl-2-methacryloxyethyl-dimethylbenzene dicarbamate, di-1-chloromethyl-2-methacryloxyethyl-dimethylcyclohexane dicarbamate, methylene-bis-1-chloromethyl-2-methacryloxyethyl4-cyclohexyl carbamate, 2,2'-bis(4-methacryloxyphenyl)propane, 2,2'bis(4-acryloxyphenyl)propane, 2,2'-bis[4(2-hydroxy-3-methacryloxy-phenyl)] propane, 2,2'-bis[4(2-hydroxy-3-acryloxy-phenyl)propane, 2,2'-bis(4-methacryloxyethoxyphenyl)propane, 2,2'-bis(4-acryloxyethoxyphenyl)propane, 2,2'-bis(4-methacryloxy-propoxyphenyl)propane, 2,2'-bis(4-acryloxypropoxyphenyl)propane, 2,2'-bis(4-methacryloxydiethoxyphenyl) propane, 2,2'-bis(4-acryloxydiethoxyphenyl)propane, 2,2'-bis[3(4-phenoxy)-2-hydroxypropane-1-methacrylate] propane, and 2,2'-bis[3(4-phenoxy)-2-hydroxypropane-1-acryalte]propane, may be mentioned.

The N-substituted alkyl acrylic or acrylic acid amide compound(s) are preferably characterized by one of the following formulae (A), (B) and (C):

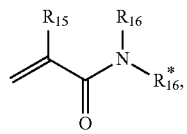

(A)

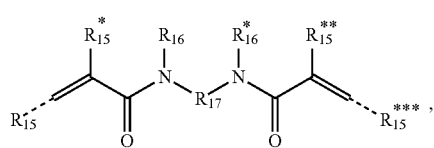

(B)

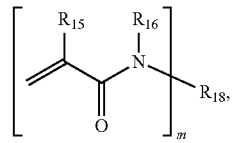

(C)

wherein $R_{15}$, $R^*_{15}$, $R^{}_{15}$, $R^{*}_{15}$ independently represent a hydrogen atom, —COOM, a straight chain or branched $C_1$ to $C_{18}$ alkyl group which may be substituted by a $C_{3-6}$ cycloalkyl group, a $C_{6-14}$ aryl or $C_{3-14}$ heteroaryl group, —COOM, —PO$_3$M, —O—PO$_3$M$_2$ or —SO$_3$M, a $C_3$ to $C_{18}$ cycloalkyl group which may be substituted by a $C_{1-16}$ alkyl group, a $C_{6-14}$ aryl or $C_{3-14}$ heteroaryl group, —COOM, —PO$_3$M, —O—PO$_3$M$_2$ or —SO$_3$M, or a $C_5$ to $C_{18}$ aryl or $C_3$ to $C_{18}$ heteroaryl group which may be substituted by —COOM, —PO$_3$M, —O—PO$_3$M$_2$ or —SO$_3$M, $R_{16}$ and $R^*_{16}$ independently represent a hydrogen atom, a straight chain or branched $C_1$ to $C_{18}$ alkyl group or $C_2$ to $C_{18}$ alkenyl group, which may be substituted by a $C_{3-6}$ cycloalkyl group, a $C_{6-14}$ aryl or $C_{3-14}$ heteroaryl group, —COOM, —PO$_3$M, —O—PO$_3$M$_2$ or —SO$_3$M, a $C_3$ to $C_{18}$ cycloalkyl group which may be substituted by a $C_{1-16}$ alkyl group, a $C_{6-14}$ aryl or $C_{3-14}$ heteroaryl group, —COOM, —PO$_3$M, —O—PO$_3$M$_2$ or —SO$_3$M, or a $C_5$ to $C_{18}$ aryl or $C_3$ to $C_{18}$ heteroaryl group which may be substituted by —COOM, —PO$_3$M, —O—PO$_3$M$_2$ or —SO$_3$M, $R_{17}$ represents a divalent substituted or unsubstituted organic residue having from 1 to 45 carbon atoms, whereby said organic residue may contain from 1 to 14 carbonyl groups or heteroatoms selected from oxygen, nitrogen and sulphur; preferably $R_{17}$ is a $C_1$ to $C_{18}$ alkylene group or a $C_2$ to $C_{18}$ alkenylene group, which may contain 1 to 6 carbonyl groups or heteroatoms selected from oxygen, nitrogen and sulfur, and which may be substituted by a hydroxyl group, a $C_{6-14}$ aryl group, —COOM, —PO$_3$M, —O—PO$_3$M$_2$ or —SO$_3$M, wherein in said $C_1$ to $C_{18}$ alkylene group and said $C_2$ to $C_{18}$ alkenylene group, from 1 to 6 —CH$_2$-groups may be replaced by a —N—(C=O)—CR$_{19}$=CH$_2$ group wherein $R_{19}$ is a hydrogen atom or a $C_1$ to $C_{18}$ alkyl group, a substituted or unsubstituted $C_3$ to $C_{18}$ cycloalkyl group, a substituted or unsubstituted $C_4$ to $C_{18}$ aryl or heteroaryl group, a substituted or unsubstituted $C_5$ to $C_{18}$ alkylaryl or alkylheteroaryl group, a substituted or unsubstituted $C_7$ to $C_{30}$ aralkyl group, and a substituted or unsubstituted $C_2$ to $C_{45}$ mono-, di- or polyether group having from 1 to 14 oxygen atoms, $R_{18}$ represents a saturated di- or multivalent substituted or unsubstituted $C_2$ to $C_{18}$ hydrocarbon group, a saturated di- or multivalent substituted or unsubstituted cyclic $C_3$ to $C_{18}$ hydrocarbon group, a di- or multivalent substituted or unsubstituted $C_4$ to $C_{18}$ aryl or heteroaryl group, a di- or multivalent substituted or unsubstituted $C_5$ to $C_{18}$ alkylaryl or alkylheteroaryl group, a di- or multivalent substituted or unsubstituted $C_7$ to $C_{30}$ aralkyl group, or a di- or multivalent substituted or unsubstituted $C_2$ to $C_{45}$ mono-, di-, or polyether residue having from 1 to 14 oxygen atoms, and m is an integer, preferably in the range from 1 to 10, wherein M of any one $R_{15}$, $R^*_{15}$, $R^{}_{15}$, $R^{*}_{15}$, $R_{16}$, $R^*_{16}$, $R_{17}$ and $R_{18}$, which M are independent from each other, each represent a hydrogen atom or a metal atom.

For $R_{16}$, $R^*_{16}$ and $R_{17}$, the term "$C_3$ to $C_{18}$ cycloalkyl group" includes polycycloalkyl groups comprising two or more cycloalkyl groups wherein at least two rings share one C—C bond. Preferred are $C_5$ to $C_{14}$ polycycloalkyl groups, more preferred are $C_8$ to $C_{12}$ polycycloalkyl groups, and most preferred are tricyclo[$5.2.1.0^{2.6}$]decyl or adamantyl.

For $R_{15}$, $R*_{15}$, $R_{15}$ and $R*_{15}$, the straight chain or branched $C_1$ to $C_{18}$ alkyl group may e.g. be methyl, ethyl, n-propyl, i-propyl, n-butyl, isobutyl, tert-butyl, sec-butyl, pentyl or hexyl. For $R_{16}$ and $R*_{16}$, the $C_{1-16}$ alkyl group or $C_{2-16}$ alkenyl group may e.g. be eth(en)yl, n-prop(en)yl, i-prop(en)yl, n-but(en)yl, isobut(en)yl, tert-but(en)yl sec-but(en)yl, pent(en)yl or hex(en)yl.

For $R_{15}$, $R*_{15}$, $R_{15}$, $R*_{15}$, $R_{16}$ and $R*_{16}$, an aryl group may, for example, be a phenyl group or a naphthyl group, and a $C_{3-14}$ heteroaryl group may contain 1 to 3 heteroatoms selected from nitrogen, oxygen and sulfur.

In compound of formula (A), $R_{16}$ and $R*_{16}$ may cooperatively form a ring in which $R_{16}$ and $R_{16}*$ are linked by a C—C bond or a functional group selected from the group consisting of an ether group, a thioether group, an amine group and an amide group.

In formula (B), the dotted bond indicates that $R_{15}$ and $R***_{15}$ may be in cis or trans configuration relative to CO.

Preferably, in formula (B), $R_{15}$, $R*_{15}$, $R_{15}$ and $R*_{15}$ independently represent a hydrogen atom, —COOM, a straight chain or branched $C_{1-16}$ alkyl group which may be substituted by a $C_{3-6}$ cycloalkyl group, a $C_{6-14}$ aryl or $C_{3-14}$ heteroaryl group, —COOM, —$PO_3M$, —O—$PO_3M_2$ or —$SO_3M$, a $C_{3-6}$ cycloalkyl group which may be substituted by a $C_{1-16}$ alkyl group, a $C_{6-14}$ aryl or $C_{3-14}$ heteroaryl group, —COOM, —$PO_3M$, —O—$PO_3M_2$ or —$SO_3M$, a $C_{6-14}$ aryl or $C_{3-14}$ heteroaryl group which may be substituted by —COOM, —$PO_3M$, —O—$PO_3M_2$ or —$SO_3M$. More preferably, in formula (B), $R_{15}$, $R*_{15}$, $R_{15}$ and $R*_{15}$ independently represent a hydrogen atom, a straight chain or branched $C_{1-8}$ alkyl group which may be substituted by a $C_{4-6}$ cycloalkyl group, a $C_{6-10}$ aryl or $C_{4-10}$ heteroaryl group, a $C_{4-6}$ cycloalkyl group which may be substituted by a $C_{1-6}$ alkyl group, a $C_{6-10}$ aryl or $C_{4-10}$ heteroaryl group or a $C_{6-10}$ aryl group. Even more preferably, $R_{15}$, $R*_{15}$, $R_{15}$ and $R*_{15}$ independently represent a hydrogen atom, a straight chain or branched $C_{1-4}$ alkyl group which may be substituted by a cyclohexyl group or a phenyl group, or a cyclohexyl group which may be substituted by a $C_{1-4}$ alkyl group. Most preferably, $R_{15}$, $R*_{15}$, $R_{15}$ and $R*_{15}$ independently represent a hydrogen atom or a straight chain or branched $C_{1-4}$ alkyl group.

Preferably, in formula (B), $R_{16}$ and $R*_{16}$ independently represent a hydrogen atom, a straight chain or branched $C_{1-16}$ alkyl group or $C_{2-16}$ alkenyl group which may be substituted by a $C_{3-6}$ cycloalkyl group, a $C_{6-14}$ aryl or $C_{3-14}$ heteroaryl group, —COOM, —$PO_3M$, —O—$PO_3M_2$ or —$SO_3M$, a $C_{3-6}$ cycloalkyl group which may be substituted by a $C_{1-16}$ alkyl group, a $C_{6-14}$ aryl or $C_{3-14}$ heteroaryl group, —COOM, —$PO_3M$, —O—$PO_3M_2$ or —$SO_3M$, a $C_{6-14}$ aryl or $C_{3-14}$ heteroaryl group which may be substituted by —COOM, —$PO_3M$, —O—$PO_3M_2$ or —$SO_3M$. More preferably, $R_{16}$ and $R*_{16}$ independently represent a hydrogen atom, a straight chain or branched $C_{1-10}$ alkyl or $C_{2-10}$ alkenyl group group which may be substituted by a $C_{4-6}$ cycloalkyl group, a $C_{6-10}$ aryl or $C_{4-10}$ heteroaryl group, a $C_{4-6}$ cycloalkyl group which may be substituted by a $C_{1-6}$ alkyl group, a $C_{6-10}$ aryl or $C_{4-10}$ heteroaryl group or a $C_{6-10}$ aryl group. Even more preferably, $R_{16}$ and $R*_{16}$ independently represent is a hydrogen atom, a straight chain or branched $C_{1-10}$ alkyl group or $C_{2-10}$ alkenyl group which may be substituted by a cyclohexyl group or a phenyl group, or a cyclohexyl group which may be substituted by a $C_{1-4}$ alkyl group. Most preferably, $R_{16}$ and $R*_{16}$ represent an unsubstituted $C_{1-10}$ alkyl group or $C_{2-10}$ alkenyl group, even more preferably an unsubstituted $C_{2-6}$ alkyl group or $C_{3-6}$ alkenyl group, most preferably an ethyl group or an allyl group.

Particular preferred mono- or bis- or (meth)acrylamides and poly[(meth) acrylamides] have the following formulae:

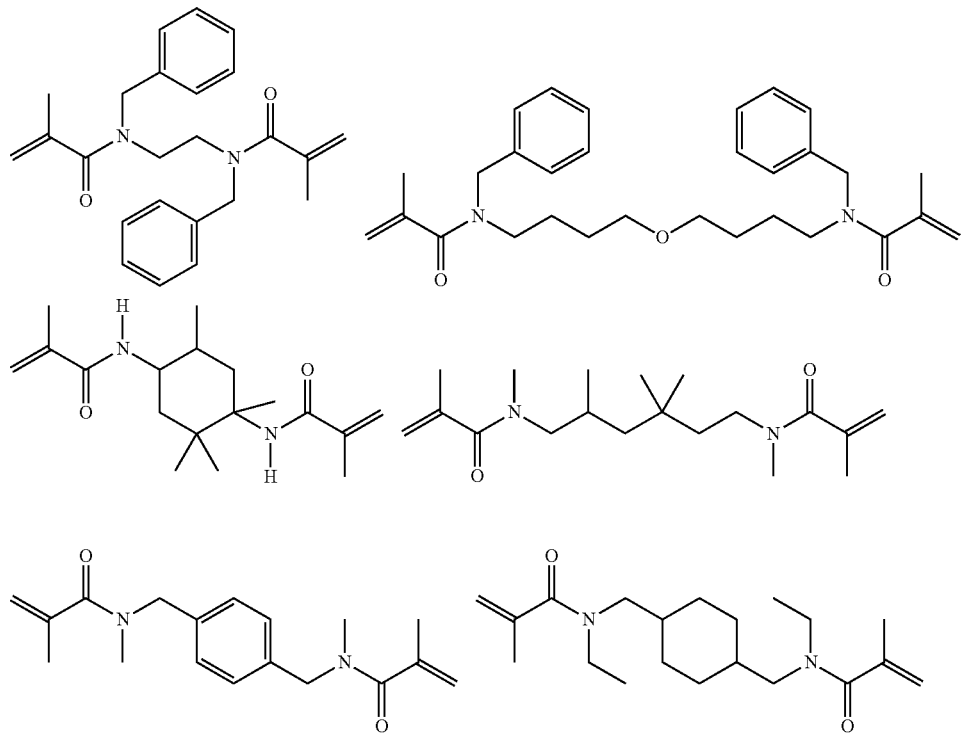

-continued
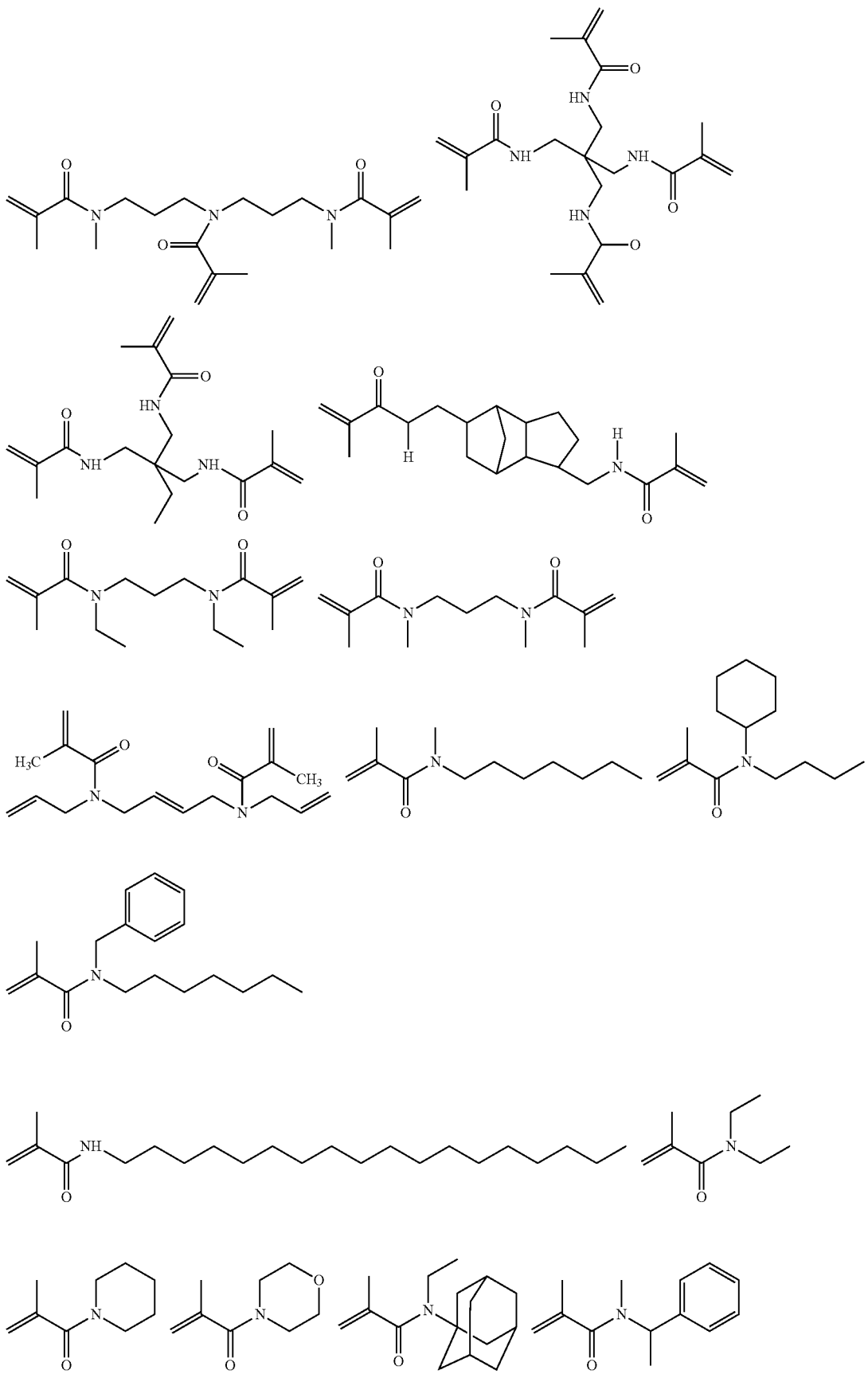

-continued
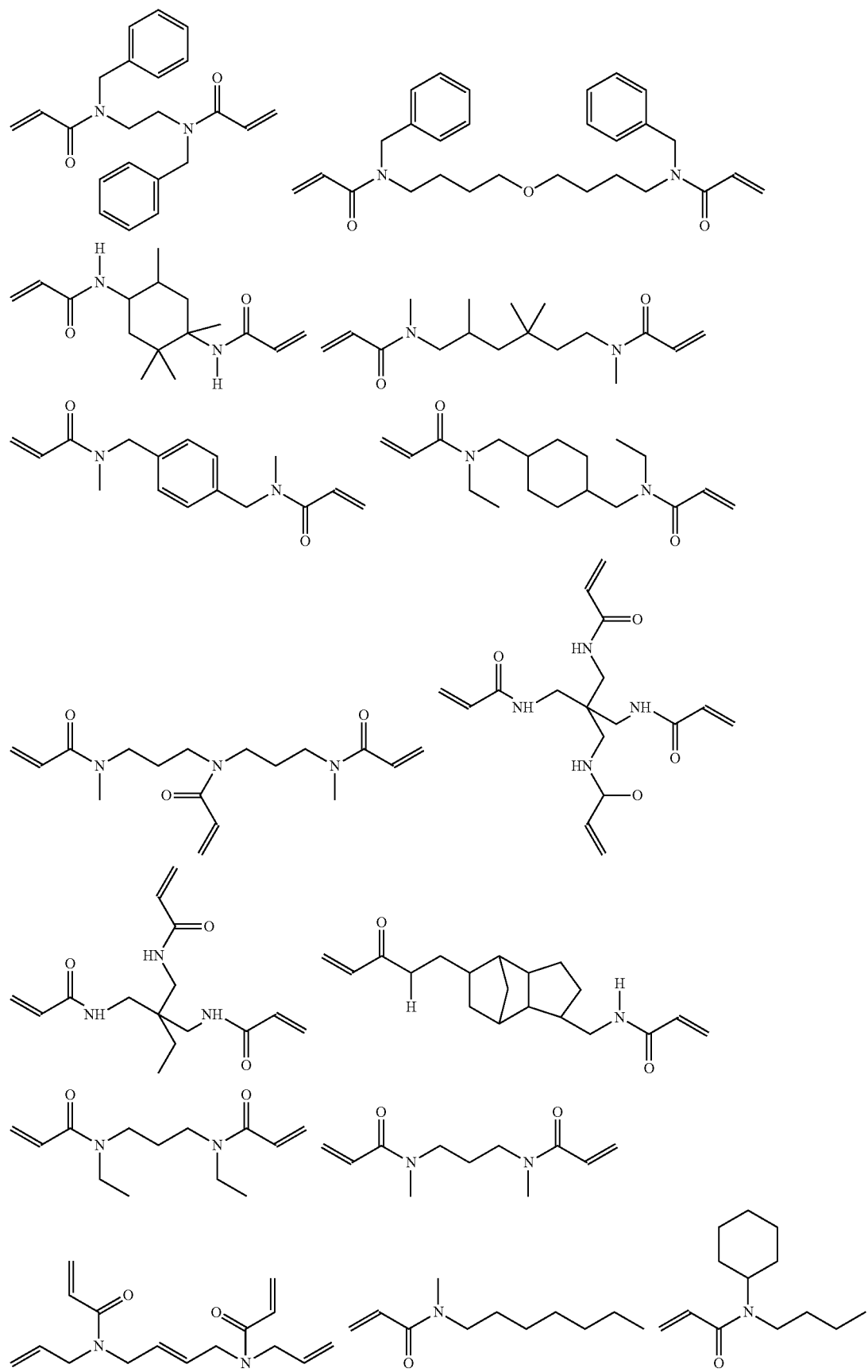

-continued

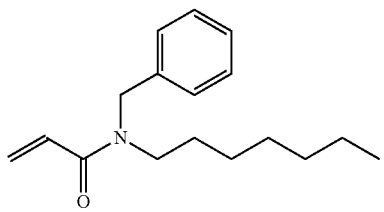

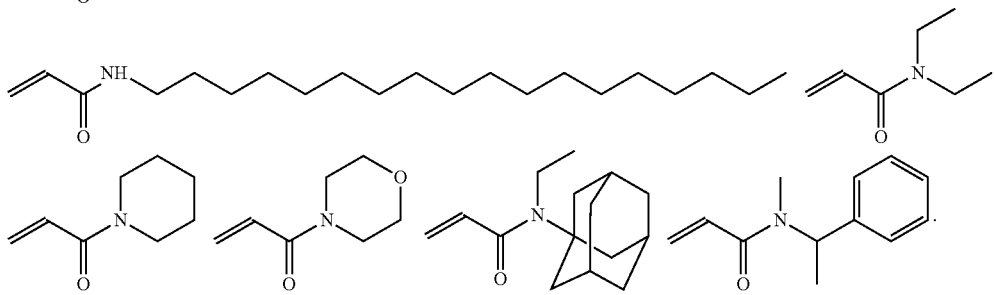

Particular preferred are the bis-(meth)acrylamides:
N,N'-diallyl-1,4-bisacrylamido-(2E)-but-2-en (BAABE) having the structural formula

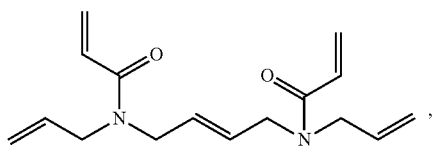 [SMILES: C=CCN(C/C=C/CN(CC=C)C(=O)C=C)C(=O)C=C]

and
N,N'-diethyl-1,3-bisacrylamido-propan (BADEP) having the structural formula

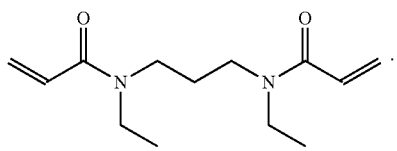 [SMILES: C=CC(=O)N(CC)CCCN(CC)C(=O)C=C]

Other suitable examples of polymerizable compounds having a polymerizable double bond are isopropenyl oxazoline, vinyl azalactone, vinyl pyrrolidone, styrene, divinylbenzene, urethane acrylates or methacrylates, epoxy acrylates or methacrylates and polyol acrylates or methacrylates.

According to a preferred embodiment, at least one of the polymerizable compounds having at least one polymerizable double bond has an acidic group. This acidic group is preferably selected from a carboxylic acid group, a sulfonic acid ester group, a phosphonic acid ester group and a phosphoric acid ester group.

Phosphoric acid ester group containing polymerizable compounds having at least one polymerizable double bond preferably have the following formula (D):

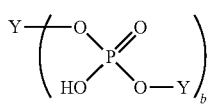
(D)

wherein
the moieties Y independent from each other represent a hydrogen atom or a moiety of the following formulae (Y*), (Y) or (Y*):

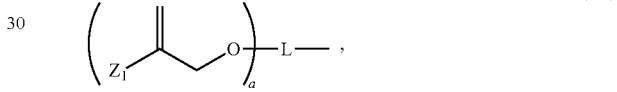
(Y*)

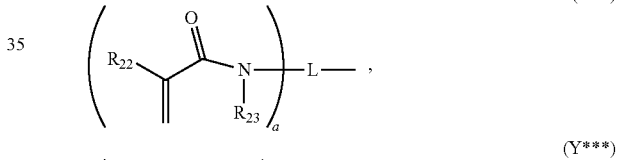
(Y**)

(Y***)

wherein
$Z_1$ is $COOR^{20}$, $COSR^{21}$, $CON(R^{20})_2$, $CONR^{20}R^{21}$, or $CONHR^{20}$, wherein $R^{20}$ and $R^{21}$ independently represent a hydrogen atom, a $C_{1-18}$ alkyl group optionally substituted by a $C_{3-8}$ cycloalkyl group, an optionally substituted $C_{3-8}$ cycloalkyl group, an optionally substituted $C_{4-18}$ aryl or heteroaryl group, an optionally substituted $C_{5-18}$ alkylaryl or alkylheteroaryl group, or an optionally substituted $C_{7-30}$ aralkyl group, whereby two $R^{20}$ residues may form together with the adjacent nitrogen atom to which they are bound a 5- to 7-membered heterocyclic ring which may contain further nitrogen atoms or an oxygen atoms, and whereby the optionally substituted groups may be substituted by 1 to 5 $C_{1-5}$ alkyl group(s);

$R_{22}$ and $R_{23}$ independently represent a hydrogen atom, an optionally substituted $C_{1-18}$ alkyl group, an optionally substituted $C_{3-18}$ cycloalkyl group, an optionally substituted $C_{5-18}$ aryl or heteroaryl group, an optionally substituted $C_{5-18}$ alkylaryl or alkylheteroaryl group, an optionally substituted $C_{7-30}$ aralkyl group, whereby the optionally substituted groups may be substituted by 1 to 5 $C_{1-5}$ alkyl group(s);

L represents an (a+b)-valent organic residue (whereby b is 1 when Y in formula (D) is within the round brackets) containing 2 to 45 carbon atoms and optionally heteroatoms such as oxygen, nitrogen and sulfur atoms, the carbon atoms including a+b carbon atoms selected from primary and secondary aliphatic carbon atoms, secondary alicyclic carbon atoms, and aromatic carbon atoms, each of said a+b carbon atoms linking a phosphate or a moiety of any one of formulae (Y*), (Y) or (Y*); a is an integer of from 1 to 10, preferably 1 to 5; b is an integer of from 1 to 10, preferably 1 to 5; provided that at least one Y is not hydrogen. The preparation of such compounds wherein Y=Y is known from EP-A 1 548 021.

The aqueous dental composition may also contain polymerizable compounds having at least one polymerizable double bond selected from the group consisting of (b1) polymerisable acidic compounds of the following formula (E):

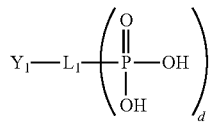

wherein
the moiety $Y_1$ represents a moiety of the following formulae $(Y_1{}^*)$, $(Y_1{}^{})$ or $(Y_1{}^{*})$:

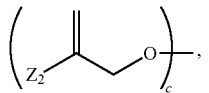

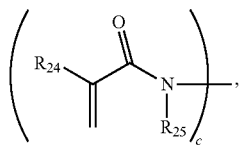

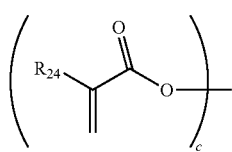

$Z_2$ independently has the same meaning as defined for $Z_1$;

$R_{24}$ and $R_{25}$ independently have the same meaning as defined for $R_{22}$ and $R_{23}$;

$L_1$ represents a (c+d) valent organic residue containing 2 to 45 carbon atoms and optionally heteroatoms such as oxygen, nitrogen and sulfur atoms, the carbon atoms including c+d carbon atoms selected from primary and secondary aliphatic carbon atoms, secondary alicyclic carbon atoms, and aromatic carbon atoms, each of said c+d carbon atoms linking a phosphonate or a moiety of any one of formulae $(Y_1{}^*)$, $(Y_1{}^{})$ or $(Y_1{}^{*})$; and c and d independently represent integers of from 1 to 10;

(b2) polymerisable acidic compounds of the following formula (F):

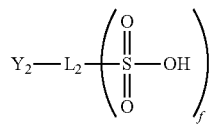

wherein
the moiety $Y_2$ represents a moiety of the following formulae $(Y_2{}^*)$, $(Y_2{}^{})$ or $(Y_2{}^{*})$:

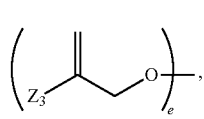

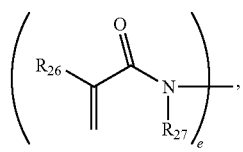

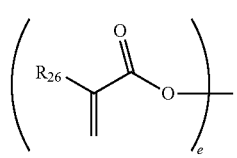

$Z_3$ independently has the same meaning as defined for $Z_1$;

$R_{26}$ and $R_{27}$ independently have the same meaning as defined for $R_{22}$ and $R_{23}$;

$L_2$ represents an (e+f) valent organic residue containing 2 to 45 carbon atoms and optionally heteroatoms such as oxygen, nitrogen and sulfur atoms, the carbon atoms including e+f carbon atoms selected from primary and secondary aliphatic carbon atoms, secondary alicyclic carbon atoms, and aromatic carbon atoms, each of said e+f carbon atoms linking a sulphonate or a moiety of any one of formulae $(Y_2{}^*)$, $(Y_2{}^{})$ or $(Y_2{}^{*})$; and e and f independently represent an integer of from 1 to 10.

It is preferred to select compounds of formula (D), (E) and (F) with the proviso that they do not contain ester groups, or at least only ester groups which do not hydrolyze in aqueous media at pH 3 at room temperature within one month, such as the phosphoric acid ester group of compounds of formula (D). Thereby, an advantageous stability of the aqueous dental composition having a pH of less than 7 in terms of shelf-life stability of the uncured dental composition as well as stability after curing in the mouth of a patient is ensured. Therefore, particularly preferred are compounds of formula (D) excluding the moiety of formula Y*** and the moiety of formula Y* wherein $Z_1$ is $COOR^{20}$ or $COSR^{21}$, compounds of formula (E) excluding the moiety of formula $Y_1{}^{***}$ and the moiety of formula $Y_1{}^*$ wherein $Z_2$ is $COOR^{20}$ or $COSR^{21}$ as well as compounds of formula (F) excluding the moiety of formula $Y_2{}^{***}$ and the moiety of formula $Y_2{}^*$ wherein $Z_3$ is $COOR^{20}$ or $COSR^{21}$.

A carboxylic acid group containing polymerizable compound having at least one polymerizable double bond may be selected e.g. from acrylic acid and methacrylic acid.

From the phosphoric acid ester group containing polymerizable compound having at least one polymerizable double bond, compounds of formula (D') characterized by one of the following formulae are particularly preferred:

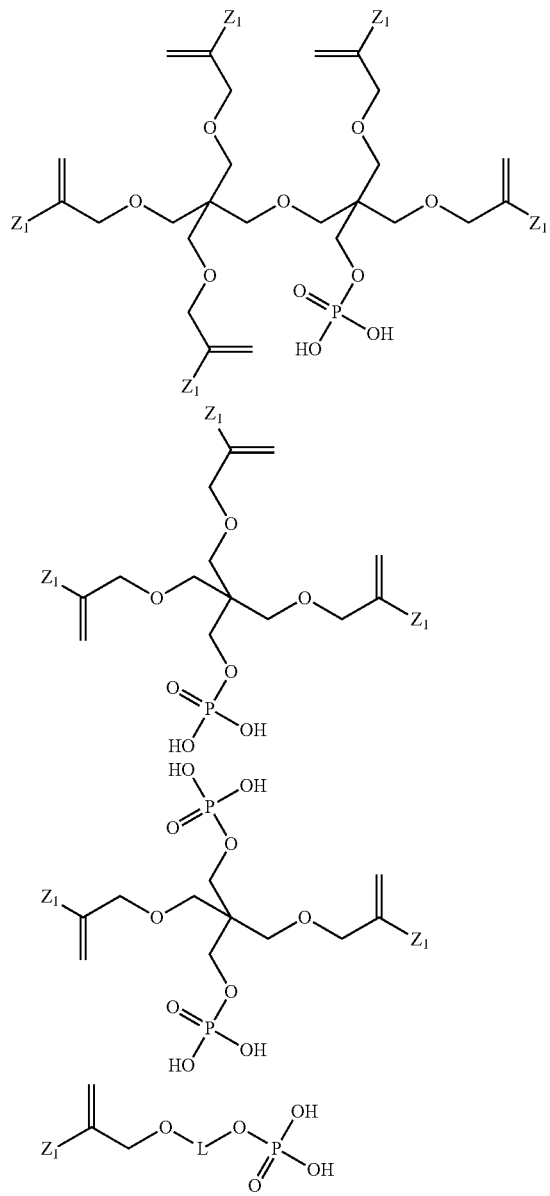

wherein $Z_1$ is defined as above, and L is an optionally substituted alkylene group. More preferably, $Z_1$ is methyl, and L is an unsubstituted alkylene group. Even more preferably, L is $C_4$ to $C_{16}$ alkylene, yet even more preferably $C_8$ to $C_{12}$ alkylene, and in particular C10 alkylene (decylene). Preferred compounds of formula (D') are dipentaerythritol pentaacrylate phosphate (PENTA) and/or 10-methacryloyloxydecyl dihydrogen phosphate (MDP), wherein MDP is most preferred.

From the sulfonic acid ester group containing polymerizable compound having at least one polymerizable double bond, compounds of formula (F') characterized by one of the following formulae are particularly preferred:

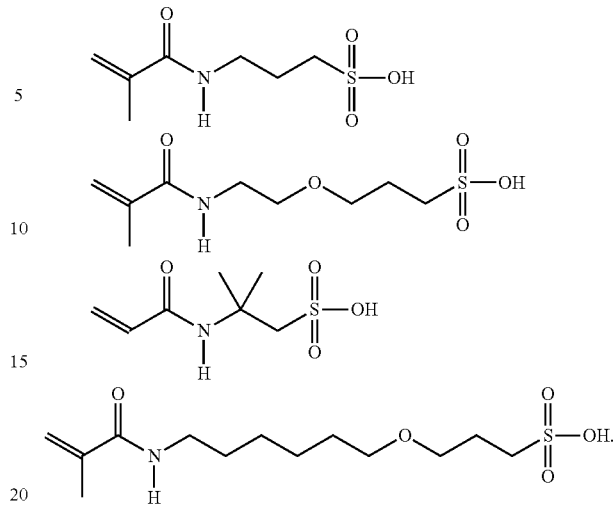

In a particularly preferred embodiment, according to (i), the aqueous dental composition according to the present invention contains at least one polymerizable compound having at least one (meth)acryl moiety and optionally at least one polymerizable compound having a polymerizable double bond and an acidic group, more preferably at least one polymerizable compound of formula (A), (B) or (C) described above and optionally at least one polymerizable compound of formula (D), (E) or (F) described above, even more preferably at least one polymerizable compound of formula (B) and optionally at least one compound of formula (D).

According to (ii), the polymerization initiator system contains
(a) an 1,2-diketone photoinitiator compound having a light absorption maximum in the range from 300 to 500 nm; and
(b) a coinitiator compound.

The polymerization initiator system may contain one or more 1,2-diketone photoinitiator(s) according to (a). The 1,2-diketone photoinitiator according to (a) belongs to the Norrish type II photoinitiators which provide free radical intermediates by photochemical abstraction. Preferably, the 1,2-diketone photoinitiator compound according to (a) is selected from the group consisting of camphorquinone, benzil, 2,2'-3 3'- and 4,4'-dihydroxylbenzil, 2,3-butanedione, 2,3-pentanedione, 2,3-hexanedione, 3,4-hexanedione, 2,3-heptanedione, 3,4-heptanedione, 2,3-octanedione, 4,5-octanedionefuril, biacetyl, 1,2-cyclohexanedione, 1,2-naphthaquinone and acenaphthaquinone.

The polymerization initiator system may contain one or more coinitiator compound(s) according to (b). The coinitiator compound according to (b) is any compound which provides for a synergistic effect in terms of photoinitiation together with the 1,2-diketone photoinitiator according to (a). The coinitiator is preferably an electron donor which may be selected from the group consisting of amines, amides, ethers, thioethers, ureas, thioureas, ferrocene, sulfinic acids and their salts, salts of ferrocyanide, ascorbic acid and its salts, dithiocarbamic acid and its salts, salts of xanthates, salts of ethylene diamine tetraacetic acid and salts of tetraphenylboronic acid. Particularly preferred donors contain an electron donor atom such as a nitrogen, oxygen, phosphorus, or sulfur atom, and an abstractable hydrogen atom bonded to a carbon or silicon atom alpha to the electron donor atom.

More preferably, the electron-donor is an amine compound, even more preferably a tertiary amine selected from the group consisting of triethanolamine, 4-N,N-dimethylaminobenzonitrile, methyl N,N-dimethylaminobenzoate, ethyl N,N-dimethylaminobenzoate, N,N-dimethylaminoethyl methacrylate and isoamyl 4-N,N-dimethylaminobenzoate, N,N-dimethylaniline, N,N-dimethyltoluidine, N,N-diethanoltoluidine, dimethylaminoanisole, 1 or 2-dimethylaminonaphthalene. In particular, the tertiary amine is selected from the group consisting of triethanolamine, methyl 4-N,N-dimethylaminobenzoate, ethyl 4-N,N-dimethylaminobenzoate, 4-N,N-dimethylaminoethyl methacrylate and isoamyl 4-N,N-dimethylaminobenzoate.

Furthermore, the polymerization initiator system may additionally comprise one or more compound(s) selected from the group consisting of iodonium-, sulfonium or phosphonium salts and aromatic tertiary phosphine compounds.

Preferably, iodonium, sulfonium or phosphonium salts are selected from the following group:

(1) an iodonium compound of the following formula (III):

$$R^7—I^+—R^8 A^-  \quad (III)$$

wherein
R$^7$ and R$^8$
which are independent from each other, represent an organic moiety, and
A$^-$ is an anion;

(2) a sulfonium compound of the following formula (IV):

$$R^9 R^{10} R^{11} S^+ A^- \quad (IV)$$

wherein
R$^9$, R$^{10}$ and R$^{11}$
which are independent from each other, represent an organic moiety or wherein any two of R$^9$, R$^{10}$ and R$^{11}$ form a cyclic structure together with the sulfur atom to which they are bound, and
A$^-$ is an anion;

(3) a phosphonium compound of the following formula (V):

$$R^{12} R^{13} R^{14} P^+ A^- \quad (V)$$

wherein
R$^{12}$, R$^{13}$ and R$^{14}$
which are independent from each other, represent an organic moiety, and
A$^-$ is an anion; and (4) a pyridinium salt.

In the iodonium compounds of formula (III), R$^7$ and R$^8$ preferably represent an aromatic, an aliphatic or an alicyclic group. An aromatic group may be a phenyl group. The phenyl group may be substituted by one or more straight chain or branched alkyl groups having 1 to 6 carbon atoms, straight chain or branched alkoxy groups having 1 to 6 carbon atoms, aromatic groups such as aryl groups or aryloxy groups, alicyclic groups having 3 to 6 carbon atoms, halogen atoms, hydroxyl groups, or amino groups. The aliphatic group may be a straight chain or branched alkyl groups having 1 to 6 carbon atoms which may be substituted by one or more aromatic groups, alicyclic groups having 3 to 6 carbon atoms, halogen atoms, hydroxyl groups or amino groups. An alicyclic group may be a group having 3 to 6 carbon atoms which may be substituted by one or more aromatic groups, aliphatic groups, halogen atoms, hydroxyl groups or amino groups.

According to a preferred embodiment, the iodonium compound of formula (III) is a diaryl iodonium salt. Examples of useful diaryl iodonium salt include (4-methylphenyl)[4-(2-methylpropyl) phenyl] iodonium hexafluoroantimonate, include (4-methylphenyl)[4-(2-methylpropyl) phenyl] iodonium tetrafluoroborate, diphenyliodonium (DPI) tetrafluoroborate, di(4-methylphenyl)iodonium (Me2-DPI) tetrafluoroborate, phenyl-4-methylphenyliodonium tetrafluoroborate, di(4-heptylphenyl)iodonium tetrafluoroborate, di(3-nitrophenyl)iodonium hexafluorophosphate, di(4-chlorophenyl)iodonium hexafluorophosphate, di(naphthyl)iodonium tetrafluoroborate, di(4-trifluoromethylphenyl)iodonium tetrafluoroborate, DPI hexafluorophosphate, Me2-DPI hexafluorophosphate; DPI hexafluoroarsenate, di(4-phenoxyphenyl)iodonium tetrafluoroborat, phenyl-2-thienyliodonium hexafluorophosphate, 3,5-dimethylpyrazolyl-4-phenyliodonium hexafluorophosphate, DPI hexafluoroantimonate, 2,2'-DPI tetrafluoroborate, di(2,4-dichlorophenyl) iodonium hexafluorophosphate, di(4-bromophenyl)iodonium hexafluorophosphate, di(4-methoxyphenyl)iodonium hexafluorophosphate, di(3-carboxyphenyl) iodonium hexafluorophosphate, di(3-methoxycarbonylphenyl)iodonium hexafluorophosphate, di(3-methoxysulfonylphenyl)iodonium hexafluorophosphate, di(4-acetamidophenyl) iodonium hexafluorophosphate, di(2-benzothienyl)iodonium hexafluorophosphate, and DPI hexafluorophosphate.

Particularly preferred iodonium compounds of formula (III) include diaryliodonium hexafluorophosphate such as diphenyliodonium (DPI) hexafluorophosphate, di(4-methylphenyl) iodonium (Me2-DPI) hexafluorophosphate, diaryliodonium hexafluoroantimonate, (4-methylphenyl)[4-(2-methylpropyl) phenyl] iodonium hexafluoroantimonate, (4-methylphenyl)[4-(2-methylpropyl)phenyl]iodonium hexafluorophosphate (Irgacure® 250, commercial product available from BASF SE), (4-methylphenyl)[4-(2-methylpropyl) phenyl] iodonium tetrafluoroborate, 4-octyloxyphenyl phenyliodonium hexafluoroantimonate, 4-(2-hydroxytetradecyloxyphenyl)phenyliodonium hexafluoroantimonate, and 4-(1-methylethyl)phenyl 4-methylphenyliodonium tetrakis(pentafluorophenyl)borate.

According to a particularly preferred embodiment, the iodonium compounds of formula (III) are selected from the group consisting of DPI hexafluorophosphate and 4-methylphenyl)[4-(2-methylpropyl)phenyl]iodonium hexafluorophosphate (Irgacure® 250, commercial product available from BASF SE).

According to a preferred embodiment, the polymerizable matrix contains the iodonium compound of the following formula (III), preferably in the form of a diphenyl iodonium (DPI) or di(4-methylphenyl)iodonium (Me2-DPI) compound, more preferably di(4-methylphenyl) iodonium (Me2-DPI), in an amount from 0.001 to 2 percent by weight based on the total weight of the composition.

A preferred sulfonium compound of the formula (IV) is S-(phenyl)thianthrenium hexafluorophosphate of the following formula:

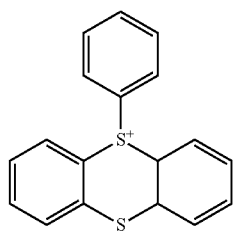

The phosphonium compound of formula (V) may be a tetrakis-(hydroxymethyl)-phosphonium (THP) salt or a tetrakis-(hydroxymethyl)-phosphonium hydroxide (THPOH) salt, wherein the anion $A^-$ is selected from the group consisting of formate, acetate, phosphate, sulphate, fluoride, chloride, bromide and iodide.

In a salt of a compound of any one of formula (III) to (VI), the anion may be an anion selected from halogenides such as chloride, bromide and iodide, hexafluorophosphate, tetrafluoroborate, tetraphenylborate, hexafluoroantimonate and trifluoromethylsulfonate.

Furthermore, the photoinitiator system may additionally comprise an aromatic tertiary phosphine compound, wherein it is preferred that the aromatic tertiary phosphine compound has the following formula (VI):

$$Z_4-R^{28} \quad\quad (VI)$$

wherein $Z_4$ is a group of the following formula (VII)

$$R^{29}(Ar)P- \quad\quad (VII)$$

wherein $R^{29}$ represents a substituted or unsubstituted hydrocarbyl group;

Ar represents a substituted or unsubstituted aryl or heteroaryl group;

$R^{28}$ is a substituted or unsubstituted hydrocarbyl group or a group $L_3Z_4$; wherein $L_3$ is a substituted or unsubstituted divalent hydrocarbyl group which may contain a linkage selected from an ether linkage, a thioether linkage, an ester linkage, an amide linkage, and a urethane linkage and $Z_4'$ has the same meaning as $Z_4$, whereby $Z_4$ and $Z_4'$ may be the same or different;

wherein the group $R^{29}$ and Ar* may be substituted by one or more groups selected from a hydroxyl group, an oxo group, a —$NR^{30}R^{31}$ group (wherein $R^{30}$ and $R^{31}$, which may be the same or different, are selected from a hydrogen atom and $C_{1-6}$ alkyl groups), a carboxyl group, and a group having a polymerizable double bond, and $R^{28}$ and $L_3$ may be substituted by one or more groups selected from a hydroxyl group, an oxo group, a —$NR^{30}R^{31}$ group (wherein $R^{30}$ and $R^{31}$, which may be the same or different, are selected from a hydrogen atom and $C_{1-6}$ alkyl groups), a carboxyl group, and a group having a polymerizable double bond.

In the aromatic tertiary phosphine compound of the formula (VI), moieties $Z_3$, $R^{29}$, Ar*, $R^{28}$ and $L_3$ may be defined as follows:

For $R^{29}$, the monovalent hydrocarbyl group may be an alkyl group, a cycloalkyl group, a cycloalkylalkyl group, an arylalkyl group or an aryl group.

Ar* represents a substituted or unsubstituted aryl or heteroaryl group. An aryl group may be selected from a phenyl group, a naphtyl group, a tolyl group, a xylyl group, and a styryl group. A heteroaryl group may be a pyridyl group.

$L_3$ is a substituted or unsubstituted divalent hydrocarbyl group which may contain a linkage selected from an ether linkage, a thioether linkage, an ester linkage, an amide linkage, and a urethane linkage. For $L_3$, the divalent hydrocarbyl group may be an alkyldiyl group, a cycloalkyldiyl group, a cycloalkylalkyl-diyl group, an arylalkyl-diyl group or an aryldiyl group. In a cycloalkylalkyl-diyl, one valency may be bonded to each of the cycloalkyl moiety or the alkyl moiety, or both valencies may be bonded to either the cycloalkyl moiety or the alkyl moiety. In a arylalkyl-diyl group, each of the aryl moiety or the alkyl moiety may be monovalent respectively, or either the aryl moiety or the alkyl moiety is divalent, while the other moiety is nonvalent. In a cycloalkylalkyl-diyl, each of the cycloalkyl moiety or the alkyl moiety may be monovalent respectively, or either the cycloalkyl moiety or the alkyl moiety is divalent, while the other moiety is nonvalent.

The following definitions apply both for the monovalent and the divalent hydrocarbyl group, therefore, for the definition of the divalent hydrocarbyl group, the suffixes "diyl" and "-diyl" are bracketed.

An alkyl(diyl) group may be straight-chain or branched $C_{1-20}$ alkyl(diyl) group, typically a $C_{1-8}$ alkyl(diyl) group. Examples for a $C_{1-6}$ alkyl(diyl) group can include linear or branched alkyl(diyl) groups having 1 to 6 carbon atoms, preferably 1 to 4 carbon atoms, for example, methyl(diyl), ethyl(diyl), n-propyl(diyl), isopropyl(diyl), n-butyl(diyl), isobutyl(diyl), sec-butyl(diyl), tert-butyl(diyl), n-pentyl (diyl), isopentyl(diyl) and n-hexyl(diyl).

A cycloalkyl(diyl) group may be a $C_{3-20}$ cycloalkyl(diyl) group. Examples of the cycloalkyl(diyl) group can include those having 3 to 14 carbon atoms, for example, cyclopropyl (diyl), cyclobutyl(diyl), cyclopentyl(diyl) and cyclohexyl (diyl). A cycloalkylalkyl(diyl) group can include those having 4 to 20 carbon atoms.

A cycloalkylalkyl(-diyl) group can include a combination of a linear or branched alkyl(diyl) group having 1 to 6 carbon atoms and a cycloalkyl(diyl) group having 3 to 14 carbon atoms. Examples of the cycloalkylalkyl(-diyl) group can for example, include methylcyclopropyl(-diyl) methylcyclobutyl(-diyl), methylcyclopentyl(-diyl), methylcyclohexyl(-diyl), ethylcyclopropyl(-diyl), ethylcyclobutyl(-diyl), ethylcyclopentyl(-diyl), ethylcyclohexyl(-diyl), propylcyclopropyl(-diyl), propylcyclobutyl(-diyl), propyl-cyclopentyl(-diyl), propylcyclohexyl(-diyl).

An arylalkyl(-diyl) group may be a $C_{7-20}$ arylalkyl(-diyl) group, typically a combination of a linear or branched alkyl(diyl) group having 1 to 6 carbon atoms and an aryl(-diyl) group having 6 to 10 carbon atoms. Specific examples of an arylalkyl(-diyl) group are a benzyl(-diyl) group or a phenylethyl(-diyl) group.

An aryl(diyl) group can include aryl(diyl) groups having 6 to 10 carbon atoms. Examples of the aryl(diyl) group are phenyl(diyl) and naphtyl(diyl). Aryl(diyl) groups may contain 1 to 3 substituents. Examples of such substituents can include halogen atoms, a cyano group, a hydroxy group, an amino group, $C_{1-6}$ alkyl groups and $C_{1-6}$ alkoxy groups. Here, illustrative of the halogen atoms can be fluorine, chlorine, bromine and iodine. The $C_{1-4}$ alkyl(diyl) groups are, for example, methyl(diyl), ethyl(diyl), n-propyl(diyl), isopropyl(diyl) and n-butyl(diyl). Illustrative of the $C_{1-4}$ alkoxy(diyl) groups are, for example, methoxy(diyl), ethoxy (diyl) and propoxy(diyl). The alkyl(diyl) moieties in these substituents may be linear, branched or cyclic.

Preferably, the hydrocarbyl group is an aryl(diyl) group selected from a phenyl(diyl) group and a naphthyl(diyl) group, which groups may optionally be substituted by one to three groups selected from halogen atoms, a cyano group, an amino group, a hydroxy group, $C_{1-6}$ alkyl groups and C1-6 alkoxy groups, or wherein the hydrocarbyl group is a non-aromatic hydrocarbyl group selected from a straight chain or branched alkyl group, a straight chain or branched alkenyl group, or a straight chain or branched alkynyl group.

The $C_{1-8}$ alkyl(diyl) group and the $C_{3-14}$ cycloalkyl(diyl) group may optionally be substituted by one or more members of the group selected from a $C_{1-4}$ alkyl group, $C_{1-4}$ alkoxy group, a phenyl group, and a hydroxy group.

Examples for a $C_{1-4}$ alkyl group can include linear or branched alkyl groups having 1 to 4 carbon atoms, for example, methyl, ethyl, n-propyl, isopropyl, n-butyl, isobutyl, sec-butyl, tert-butyl. Examples for an $C_{1-4}$ alkoxy group can include linear or branched alkoxy groups having 1 to 4 carbon atoms, for example, methoxy, ethoxy, n-propoxy, isopropoxy, n-butoxy, isobutoxy, sec-butoxy, and tert-butoxy.

Moreover, in formula (VI), any of the hydrocarbyl group may be substituted by one or more groups selected from halogen atoms, a cyano group, an amino group or a hydroxy group. Accordingly, in the hydrocarbyl groups some or all hydrogen atoms are replaced by halogen atoms (e.g., fluoro, bromo, chloro), for example, halo-substituted alkyl groups such as chloromethyl, chloropropyl, bromoethyl and trifluoropropyl, and cyanoethyl.

In case the hydrocarbyl group contains an alkyl(diyl) chain, one or more carbon atoms in the alkyl(diyl) chain may be replaced by an oxygen atom, a sulfur atom, an amide group, an ester group, or a urethane group. In case the hydrocarbyl group is an alkyl group having more than one carbon atom, the alkyl group contains an alkylene. Accordingly, in case the hydrocarbyl group is an n-hexyl group, any of the carbon atoms of the alkylene chain excluding the terminal methyl group may be replaced by an oxygen atom, a sulfur atom, an amide group, an ester group, a urethane group or an NH group. Therefore, the following groups may be given as specific examples in case of one or more oxygen atoms:

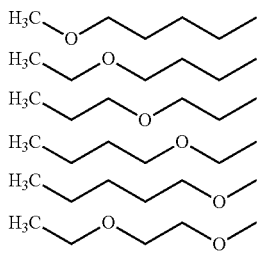

In formula (VI), group $R^{29}$ and/or Ar* as well as $R^{28}$ and/or $L_3$ may be substituted with a polymerizable double bond, preferably a carbon-carbon double bond. Examples of polymerizable carbon-carbon double bonds include vinyl, conjugated vinyl, allyl, acryl, methacryl and styryl. Preferably, the polymerizable double bond is selected from the group consisting of methacryl, acryl and styryl. More preferably, the double bond is styryl.

Preferably, $R^{29}$ and Ar* independently are aromatic hydrocarbyl groups selected from a phenyl group, a naphtyl group, a tolyl group, a xylyl group, and a styryl group.

As regards $R^{28}$, this moiety is preferably an aryl group, which may be substituted by one or more groups selected from a hydroxyl group, an amino group, a $—NR^{30}R^{31}$ group (wherein $R^{30}$ and $R^{31}$, which may be the same or different, are selected from $C_{1-6}$ alkyl groups), a carboxyl group, and a group having a polymerizable double bond. Alternatively, $R^{28}$ is preferably a group $L_3Z_4'$ wherein $Z_4'$ and $Z_4$ are the same.

More preferably, $R^{28}$ is a $C_{1-6}$ alkyl group or a $C_{1-6}$ alkenyl group, which groups may be substituted by one or more groups selected from a hydroxyl group, an amino group, a $—NR^{30}R^{31}$ group (wherein $R^{30}$ and $R^{31}$, which may be the same or different, are selected from $C_{1-6}$ alkyl groups), a carboxyl group, and a group having a polymerizable double bond. The group having a polymerizable double bond may be vinyl group, an allyl group, a (meth) acryloyloxy group or a (meth) acryloylamido group.

Even more preferably, the aromatic phosphine compound is a compound of formula (VI) wherein $Z_4$ is a group of the following formula:

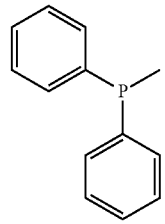

Specific examples for a compound of formula (VI) include triphenyl phosphine (TPP), 4-(diphenylphosphino) styrene (DPPS), 4-(diphenylphosphino)benzoic acid, 4-(diphenylphosphino) benzoic acid, 3-(diphenylphophonino) propionic acid, (4-(diphenylphosphino) N,N'-dimethylaniline, 2,2'-bis(diphenylphosphino)benzophenone (BDPPEP), bis[2-(diphenylphosphino)phenyl]ether (BDPPE), (4-Hydroxyphenyl) diphenylphosphine, allyldiphenylphosphine. Preferably, the compound of formula (VI) is triphenyl phosphine (TPP) or 4-(diphenylphosphino)styrene (DPPS), more preferably 4-(diphenylphosphino)styrene (DPPS).

It was surprisingly found that aromatic tertiary phosphine compounds of formula (VI) provide for both an advantageous efficiency in terms of a higher polymerisation rate and a higher final conversion rate compared to a dental composition comprising a polymerization initiator system without an aromatic tertiary phosphine compound of formula (VI). Advantageously, the polymeriation rate may be adjusted within a range which still provides for corrections when applying the aqueous dental composition to a patient's tooth or when forming a prosthesis. Although photopolymerization is achieved at a higher polymerisation and conversion rate, owing to the present polymerization initiator system, undesired side reaction resulting e.g. in discoloration of the cured dental composition can be effectively suppressed. Besides, by adding an aromatic tertiary phosphine compound of formula (VI) to the present polymerization initiator system, a yellow coloration of the aqueous dental composition eventually formed already before light curing can efficiently be reduced/decreased. That is, there is a photobleaching effect which provides for an advantageous effective reduction/decrease of yellow discolorations of the aqueous dental composition, while the initiator system furthermore provides for an advantageous polymerization and conversation rate throughout the whole course of time of the photopolymerization.

A further positive effect associated with the application of aromatic tertiary phosphines of formula (VI) as additional component of the photoinitiator system is that they provide for aqueous dental compositions exhibiting an advantageous storage stability, that is the compositions keep the characteristics of an advantageous efficiency in terms of a higher polymerisation rate and a higher final conversion rate even after a long storage time, e.g. about 2 month.

According to a particularly preferred embodiment, the polymerization initiator system according to (ii) comprises (a) a 1,2-diketone photoinitiator compound selected from camphorquinone and/or 1,2-diphenylethane-1,2-dione, and (b) the coinitiator is an amine, preferably dimethylaminobenzonitrile (DMABN).

The aqueous dental composition according to the invention may contain the polymerization initiator system in an amount of preferably from 0.01 to 10 percent by weight, preferably 0.05 to 7 percent by weight, more preferably 0.1 to 5 percent by weight based on the total weight of the aqueous dental composition. An amount of less than 0.01 percent by weight of polymerization initiator system might not provide a sufficient polymerisation rate for photocuring. An amount beyond the maximum threshold of 10 percent by weight might give rise to problems in applying the aqueous dental composition, since polymerisation rate during photocuring might be too fast, which means there is no or almost no time frame for correcting the contouring of the aqueous dental composition applied to e.g. a fissure or cavity in a tooth.

According to (iv), the aqueous dental composition of the present invention comprises a solvent mixture comprising water and an organic solvent. The solvent mixture may comprise one or more organic solvent(s).

The term "organic solvent" as used herein means any organic compound which is fluid or liquid at room temperature and which is capable of dissolving or at least partly dissolving the components according to (i), (ii) and (iii) of the present aqueous dental composition. The organic solvent is suitably selected in view of its volatility and physiological harmlessness. Preferably, the organic solvent is more volatile than water, that is it has a vapour pressure higher than water at 20° C. Besides, it is preferred that the organic solvent is non-toxic for the patient to be treated, in particular for a human patient.

According to (iv), the solvent mixture comprises water in an amount at least 1 percent by weight, preferably more than 10 percent by weight based on the total weight of the aqueous dental composition.

Surprisingly, with a water content of more than 10 percent by weight based on the total weight of the aqueous dental composition, with the aqueous dental composition according to the invention, advantageous rheological properties and/or viscosity can be obtained, which provide for a convenient application of the aqueous dental composition.

This finding is in contrast to 2006/0069181 A1, which teaches that for attaining specific rheological properties and/or viscosity, the water content mandatory has to be 0.1 to 10 weight % of the dental composition. Because, according to 2006/0069181 A1, with higher water contents, the viscosity may become too low and the desired viscosity and/or shear thinning behaviors cannot readily be obtained.

Generally, it is preferred that the solvent mixture (iv) comprises water within a value range of 2 to 60 percent by weight, more preferably 5 to 40 percent by weight, most preferably more than 10 to 30 percent by weight of water based on the total weight of the aqueous dental composition.

It is particularly preferred that the solvent mixture (iv) comprises water with a value range having a lower limit of more than 10 percent by weight, namely more than 10 to 60 percent by weight, preferably 12 to 55 percent by weight, more preferably 14 to 50 percent by weight, most preferably 16 to 40 percent by weight of water based on the total weight of the aqueous dental composition.

It is preferred that according to (iv), the organic solvent of the solvent mixture is comprised in the aqueous dental composition in an amount of at least 5 percent by weight, more preferably 8 to 40 percent by weight, even more preferably 10 to 30 percent by weight based on the total weight of the aqueous dental composition.

Furthermore, it is preferred that in the solvent mixture according to (iv), the weight ratio of organic solvent to water is 100:1 to 1:100, preferably 10:1 to 1:10, more preferably 5:1 to 1:5 and even more preferably 2:1 to 1:2.

Suitable organic solvents may be selected from alcohols such as methanol, ethanol, propanol (n-, i-), butanol (n-, iso-, tert.-), ketones such as acetone, methyl ethyl ketone or the like. Preferably, the organic solvent is propanol, more preferably isopropanol.

The aqueous dental composition of the present invention may preferably comprise 5 to 75 percent by weight based on the total weight of the composition of the solvent mixture according to (iv).

Furthermore, the aqueous dental compositions of the present invention may further comprise a particulate filler. The aqueous dental compositions of the present invention may comprise one or more particulate filler(s).

Suitable particulate fillers may be selected from fillers currently used in dental compositions. The filler should be finely divided and preferably has a maximum particle diameter less than about 100 μm and an average particle diameter less than about 10 μm. The filler may have a unimodal or polymodal (e.g., bimodal) particle size distribution.

The filler can be an inorganic material. It can also be a crosslinked organic material that is insoluble in the polymerizable resin, and is optionally filled with inorganic filler. The filler can be radioopaque. Examples of suitable particulate inorganic fillers are naturally-occurring or synthetic materials such as quartz, nitrides such as silicon nitride, glasses derived from, for example Ce, Sb, Sn, Zr, Sr, Ba and Al, colloidal silica, feldspar, borosilicate glass, kaolin, talc, titania, and zinc glass, and submicron silica particles such as pyrogenic silicas. Examples of suitable non-reactive organic filler particles include filled or unfilled pulverized polycarbonates or polyepoxides. Preferably the surface of the filler particles is treated with a coupling agent in order to enhance the bond between the filler and the matrix. The use of suitable coupling agents include gamma-methacryloxypropyltrimethoxysilane, gamma-mercaptopropyltriethoxysilane, gamma-aminopropyltrimethoxysilane, and the like.

The particulate filler may also be a filler obtainable by a process for the preparation of composite filler particles, comprising:

1) coating a particulate filler having a median particle size (D50) of from 1 to 1200 nm with a coating composition containing a film-forming agent forming a coating layer on the surface of the particulate filler, said coating layer displaying reactive groups on the surface of the coating layer, said reactive groups being selected from addition polymerizable groups and step-growth polymerizable groups, thereby forming a coated particulate filler; subsequently or concurrently 2) agglomerating the coated particulate filler, optionally in the presence of a further crosslinking agent and optionally in the presence of a further particulate filler not displaying reactive groups, for providing a granulation of the coated particulate filler wherein the granulation contains the coated particulate filler particles and the optional further particulate filler particles separated from and connected to each other by at least one coating layer, whereby the at least one coating layer may be crosslinked by crosslinking groups obtained by reacting the reactive groups and optionally a further crosslinking agent;

3) optionally milling, classifying and/or sieving the granulation of the coated particulate filler; and 4) optionally further crosslinking the granulation of the coated particulate filler; for providing composite filler particles having a median particle size (D50) of from 1 to 70 µm, wherein reactive groups are transformed into crosslinking groups obtained by reacting reactive groups and optionally a further crosslinking agent, and wherein the particulate filler is the main component by volume of the composite filler particles as further described in EP-A 2 604 247.

The aqueous dental composition of the present invention may preferably comprise 0.1 to 85 percent by weight based on the total weight of the composition of particulate filler.

The aqueous dental compositions of the present invention may contain further components such as preservatives, pigments, free radical scavengers, polymerization inhibitors, reactive and nonreactive diluents, coupling agents to enhance reactivity of fillers, rheology modifiers, and surfactants.

Suitable preservatives may be selected from reducing agents such as vitamin C, inorganic sulphides, polysulfides and the like.

Preferably, the aqueous dental composition according to any one of the preceding claims is stable at 50° C. for at least 30 days, or at 60° C. or 70° C. for at least 3 days.

The present aqueous dental composition may be provided as a one or more part composition. However, it is preferred that is provided in the form of a one-part composition.

The present aqueous dental composition may be selected from the group consisting of a dental composite composition, a resin modified dental cement, a pit and fissure sealant, a desensitizer, a protective varnish and a dental adhesive composition. The aqueous dental composition may be cured by irradiation of actinic radiation. Preferably, the present aqueous dental composition is a dental adhesive composition.

Preferably, the aqueous dental composition according to the invention has a color stability as determined according to ISO 7491:2000(en).

For the aqueous dental composition according to the invention, it is preferred that carboxylic acid functional polymer(s) are excluded. More preferably, carboxylic acid functional polymer(s) in the form of homopolymers and copolymers of unsaturated mono-, di-, or tricarboxylic acids and/or their anhydrides optionally substituted with at least one ethylenically unsaturated group. Even more preferably, carboxylic acid functional polymer(s) are excluded having the following formula:

wherein B represents an organic backbone, each X independently is a carboxylic group, each Y independently is a polymerizable group, m is a number having an average value of 2 or more, and n is a number having an average value of 0 or more. In the compound of formula $B(X)_m(Y)_n$, the backbone B may represent an oligomeric or polymeric backbone of carbon-carbon bonds, optionally containing substituents which do not unduly interfere with the polymerization reaction, such as oxygen, nitrogen or sulfur heteroatoms, Y groups include substituted and unsubstituted acrylates, methacrylates, alkenes and acrylamides, and the weight average molecular weight is at least about 250, preferably between about 500 and 500,000 and more preferably between about 1,000 and 100,000.

Such carboxylic acid functional polymer(s) do not represent a suitable component for the aqueous dental composition according to the invention, but are applied in dental compositions in the form of adhesive compositions, preferably self-etching adhesives requiring specific rheological properties and/or viscosity. For attaining these specific rheological properties and/or viscosity, US 2006/0069181 A1 teaches that these carboxylic acid functional polymer(s), in combination with 0.1 to 10 wt.-% of water based on the total weight of the dental composition provide for increased viscosities and/or shear thinning behavior compared to compositions known from the art.

Owing to the special combination of components of the present aqueous dental composition, it can be dispensed with such carboxylic acid functional polymer(s), since advantageous rheological properties and/or viscosities can be attained without such carboxylic acid functional polymer(s).

According to a particularly preferred embodiment, the aqueous dental composition having a pH of less than 7 comprises (i) one or more polymerizable compounds having at least one polymerizable double bond, preferably at least one polymerizable compound having at least one (meth) acryl moiety and optionally at least one polymerizable compound having at least one polymerizable double bond and an acidic group; more preferably at least one polymerizable compound of formula (A), (B) or (C) described above and optionally at least one polymerizable compound of formula (D), (E) or (F) described above, even more preferably at least one polymerizable compound of formula (B) described above and optionally at least one polymerizable compound of formula (D) described above; most preferably at least N,N'-diallyl-1,4-bisacrylamido-(2E)-but-2-en (BAABE) and/or N,N'-diethyl-1,3-bisacrylamido-propan (BADEP) and optionally 10-methacryloyloxydecyl dihydrogen phosphate (MDP) and/or dipentaerythritol pentaacrylate phosphate (PENTA), preferably MDP;

(ii) a polymerization initiator system containing (a) camphor quinone (CQ) as an 1,2-diketone photoinitiator compound having a light absorption maximum in the range from 300 to 500 nm; and (b) a coinitiator compound in the form of an amine, preferably dimethylamino benzonitrile (DMABN);

(c) optionally an iodonium compound of the following formula (III):

wherein $R^{7'}$ and $R^{8'}$, which are independent from each other, represent an a phenyl group which may be substituted by one or more straight chain or branched alkyl groups having 1 to 6 carbon atoms or straight chain or branched alkoxy groups having 1 to 6 carbon atoms, and $A'^-$ is hexafluoroantimonate or hexafluorophosphate;

(iii) 0.001 to 1 percent by weight, preferably 0.05 to 1.0 percent by weight, more preferably 0.075 to 0.9 percent by weight, and most preferably 0.1 to 0.8 percent by weight based on the total weight of the aqueous dental composition, of stabilizer of the following formula (I) and/or (II):

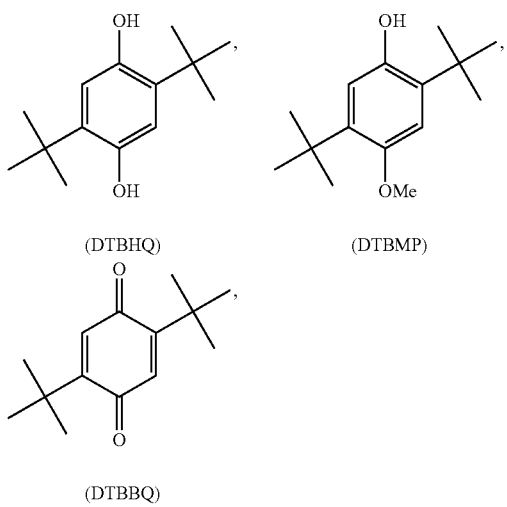

(DTBHQ)    (DTBMP)

(DTBBQ)

preferably DTBHQ and/or (DTBBQ), more preferably DTBHQ, (iv) a solvent mixture comprising an organic solvent and at least 1 percent by weight of water, preferably more than 10 percent by weight based on the total weight of the aqueous dental composition, preferably the organic solvent is an alcohol, more preferably an alcohol selected from the group of methanol, ethanol, propanol (n-, i-) and butanol (n-, iso-, tert-), even more preferably the alcohol is iso-propanol.

As regards the use of a stabilizer of the formulae (I) and (II), the stabilizer may be used for the preparation of any one of the above described aqueous dental compositions having a pH of less than 7.

The invention will now be further illustrated with reference to the following examples

EXAMPLES

Preparation of Aqueous Dental Compositions

A series of aqueous dental compositions A1, A2, A3, B1, B2, B3, C1, C2 and C3 having a composition according to Tables 1 to 3 was prepared. Each composition contains a stabilizer selected from hydroquinone (HQ), hydroquinone monomethyl ether (MeHQ), tert-butyl-hydroquinone (TBHQ) and 2,5-di-tert-butyl-hydroquinone (DTBHQ), the structure of which is depicted below. In A1, B1 and C1, a stabilizer is contained in an amount of 0.05 wt.-%. In A2, B2 and C2, a stabilizer is contained in an amount of 0.1 wt.-%, and in A3, B3 and C3, a stabilizer is contained in an amount of 0.4 wt.-%.

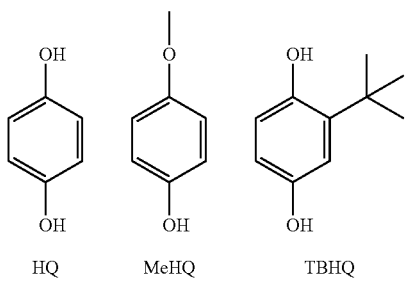

HQ    MeHQ    TBHQ

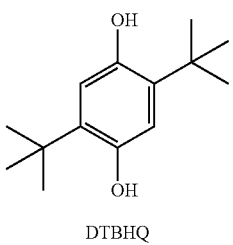

DTBHQ

HQ, MeHQ and TBHQ are not according to the present invention. DTBHQ is a stabilizer (ii) of formula (I) according to the invention.

TABLE 1

Compositions of A1, A2 and A3. Each composition was prepared with one of HQ, MeHQ, TBHQ and DTBHQ as the stabilizer, respectively.

| Testing Liquid: | | A1 | A2 | A3 |
|---|---|---|---|---|
| Dipentaerythritol pentaacrylate phosphate (PENTA) | wt-% | 0.000 | 0.000 | 0.000 |
| N,N'-(2E)-but-2-en-1,4-diallylbis-[(N-prop-2-en-1) amide (BAABE) | wt-% | 44.478 | 44.456 | 44.322 |
| N,N'-Diethyl-1,3-propylene bisacrylamide (BADEP) | wt-% | 3.898 | 3.896 | 3.884 |
| 10-Methacryloyl oxydecyl dihydrogen phosphate (MDP) | wt-% | 10.995 | 10.989 | 10.956 |
| Propan-2-ol | wt-% | 16.492 | 16.484 | 16.434 |
| Water | wt-% | 20.990 | 20.979 | 20.916 |
| Camphor quinone | wt-% | 1.799 | 1.798 | 1.793 |
| Dimethylamino benzonitrile | wt-% | 0.599 | 0.599 | 0.598 |
| Bis(4-methylphenyl)iodonium hexafluorophosphate | wt-% | 0.699 | 0.699 | 0.697 |
| Stabilizer | wt-% | 0.050 | 0.100 | 0.400 |
| Sum | wt-% | 100.000 | 100.000 | 100.000 |

TABLE 2

Compositions of B1, B2 and B3. Each composition was prepared with one of HQ, MeHQ, TBHQ and DTBHQ as the stabilizer, respectively.

| Testing Liquid: | | B1 | B2 | B3 |
|---|---|---|---|---|
| Dipentaerythritol pentaacrylate phosphate (PENTA) | wt-% | 6.497 | 6.494 | 6.474 |
| N,N'-(2E)-but-2-en-1,4-diallylbis-[(N-prop-2-en-1) amide (BAABE) | wt-% | 47.476 | 47.452 | 47.310 |
| N,N'-Diethyl-1,3-propylene bisacrylamide (BADEP) | wt-% | 5.397 | 5.395 | 5.378 |
| 10-Methacryloyl oxydecyl dihydrogen phosphate (MDP) | wt-% | 0.000 | 0.000 | 0.000 |
| Propan-2-ol | wt-% | 16.492 | 16.484 | 16.434 |
| Water | wt-% | 20.990 | 20.979 | 20.916 |
| Camphor quinone | wt-% | 1.799 | 1.798 | 1.793 |
| Dimethylamino benzonitrile | wt-% | 0.599 | 0.599 | 0.598 |
| Bis(4-methylphenyl)iodonium hexafluorophosphate | wt-% | 0.700 | 0.699 | 0.697 |
| Stabilizer | wt-% | 0.050 | 0.100 | 0.400 |
| Sum | wt-% | 100.000 | 100.000 | 100.000 |

TABLE 3

Compositions of C1, C2 and C3. Each composition was prepared with HQ, MeHQ, TBHQ and DTBHQ as the stabilizer, respectively.

| Testing Liquid: | | C1 | C2 | C3 |
|---|---|---|---|---|
| Dipentaerythritol pentaacrylate phosphate (PENTA) | wt-% | 4.398 | 4.396 | 4.382 |
| N,N'-(2E)-but-2-en-1,4-diallylbis-[(N-prop-2-en-1) amide (BAABE) | wt-% | 41.978 | 41.958 | 41.832 |
| N,N'-Diethyl-1,3-propylene bisacrylamide (BADEP) | wt-% | 3.498 | 3.496 | 3.486 |
| 10-Methacryloyl oxydecyl dihydrogen phosphate (MDP) | wt-% | 9.495 | 9.491 | 9.462 |
| Propan-2-ol | wt-% | 16.492 | 16.484 | 16.434 |
| Water | wt-% | 20.990 | 20.979 | 20.916 |
| Camphor quinone | wt-% | 1.799 | 1.798 | 1.793 |
| Dimethylamino benzonitrile | wt-% | 0.600 | 0.599 | 0.598 |
| Bis(4-methylphenyl)iodonium hexafluorophosphate | wt-% | 0.700 | 0.699 | 0.697 |
| Stabilizer | wt-% | 0.050 | 0.100 | 0.400 |
| Sum | wt-% | 100.000 | 100.000 | 100.000 |

A set of 36 aqueous dental compositions was prepared. In addition, the 12 aqueous dental compositions C1, C2 and C3 with the four different stabilizers were prepared in duplicate.

Testing of Storage Stability

For the set of 36 aqueous dental compositions, storage stability was tested for 3 days (72 h) at 60° C. to accelerate ageing and demonstrate discoloration behavior after storage. For the duplicate of 12 samples of testing liquids C1, C2 and C3, an additional storage stability test was carried out for 3 days (72 h) at 70° C.

After 3 days (72 h) at 60 or 70° C., discoloration was determined visually and documented by digital photography under yellow light. Discoloration was evaluated on the basis of the following:

(+)=no discoloration, (−)=slight discoloration, and (−−)=strong discoloration.

Discolorations denoted with (−) and (−−) are not acceptable.

Besides, in some samples, premature undesired polymerization occurred, which is denoted with (P). In case such undesired polymerization occurred, the stabilizer performance was insufficient upon high temperature storage.

The results of the storage stability testings are listed in Tables 4 and 5.

TABLE 4

Stability testing results at 60° C. for 3 d for testing liquids A1, A2, A3, B1, B2 and B3

| (stabilizer indicated below) | A1 | A2 | A3 | B1 | B2 | B3 |
|---|---|---|---|---|---|---|
| Hydroquinone (HQ) | − | − − | − − | − | − − | − |
| Hydroquinone monomethylether (MeHQ) | + | + | + | +P | −P | − −P |
| tert-Butyl-hydroquinone (TBHQ) | − | − − | − − | − − | − − | − − |
| 2,5-di-tert-Butyl-hydroquinone (DTBHQ) | + | + | + | − | + | + |

TABLE 5

Stability testing results at 60° C. and 70° C. for 3 d for testing liquids C1, C2 and C3

| | Testing Liquid: | | | | | |
|---|---|---|---|---|---|---|
| (stabilizer indicated below) | C1 | C2 | C3 | C1 | C2 | C3 |
| | at 60° C. | | | at 70° C. | | |
| Hydroquinone (HQ) | + | − | − | − | − − | − − |
| Hydroquinone monomethylether (MeHQ) | − | − | − | − | − | + |
| tert-Butyl-hydroquinone (TBHQ) | − − | − − | − − | − −P | − − | − − |
| 2,5-di-tert-Butyl-hydroquinone (DTBHQ) | − | + | + | + | + | + |

The results of the storage stability tests show that with an aqueous dental composition according to the present invention comprising 2,5-di-tert-butyl-hydroquinone DTBHQ as a stabilizer, an advantageous storage stability can be attained, since an undesired discoloration can efficiently be suppressed despite the use of propan-2-ol as a solvent. This is supported by the storage stability testing results obtained with compositions A1, A2, A3, B1, B2, B3, C1, C2 and C3 tested at 60° C., and the results obtained with compositions C1, C2 and C3 at 70° C. HQ, MeHQ and TBHQ, which are not according to the invention, do not provide satisfactory storage stability. Rather discoloration, and undesired polymerization may occur when propan-2-ol is used as a solvent.

The invention claimed is:

1. An aqueous dental composition having a pH of less than 7 comprising
 (i) a bis(meth)acrylamide compound;
 (ii) a polymerization initiator system containing
  (a) an 1,2-diketone photoinitiator compound having a light absorption maximum in the range from 300 to 500 nm; and
  (b) a coinitiator compound;
 (iii) a stabilizer of the following formula (I) and/or (II):

(I)

(II)

wherein
 the R, which may be the same or different, independently represent a branched $C_{3-8}$ alkyl or alkenyl group, or a $C_{3-8}$ cycloalkyl or cycloalkenyl group,
 R' represents a hydrogen atom, a $C_{1-6}$ alkyl or $C_{2-6}$ alkenyl group, or a $C_{1-6}$ fluoroalkyl or $C_{2-6}$ fluoroalkenyl group, X represents a group selected from a $C_{1-8}$ alkyl group or a $C_{3-8}$ cycloalkyl group, and n is 0, 1 or 2; and (iv) a solvent mixture comprising an organic solvent and more than 10 percent by weight of water based on the total weight of the aqueous dental composition;

wherein the aqueous dental composition has storage stability for at least 3 days at 60° C. or 70° C.

2. The aqueous dental composition according to claim 1, wherein the stabilizer is a compound of the following formula (Ia), (Ib) or (IIa):

(Ia)

(Ib)

(IIa)

wherein the $R^1$, $R^2$, $R^3$, $R^4$, $R^5$ and $R^6$, which may be the same or different, independently represent a methyl or an ethyl group.

3. The aqueous dental composition according to claim 1, wherein the polymerization initiator system further comprises one or more compounds selected from the following group:

(1) an iodonium compound of the following formula (III):

$$R^7\text{—}I^+\text{—}R^8 A^- \quad (III)$$

wherein $R^7$ and $R^8$
  which are independent from each other, represent an organic moiety, and $A^-$ is an anion;

(2) a sulfonium compound of the following formula (IV):

$$R^9 R^{10} R^{11} S^+ A^- \quad (IV)$$

wherein $R^9$, $R^{10}$ and $R^{11}$
  which are independent from each other, represent an organic moiety or wherein any two of $R^9$, $R^{10}$ and $R^{11}$ form a cyclic structure together with the sulfur atom to which they are bound, and $A^-$ is an anion;

(3) a phosphonium compound of the following formula (V):

$$R^{12} R^{13} R^{14} P^+ A^- \quad (V)$$

wherein $R^{12}$, $R^{13}$ and $R^{14}$
  which are independent from each other, represent an organic moiety, and $A^-$ is an anion; and (4) a pyridinium salt.

4. The aqueous dental composition according to claim 1, wherein the organic solvent is isopropanol.

5. The aqueous dental composition according to claim 1, wherein the 1,2-diketone photoinitiator compound is selected from camphorquinone and 1,2-diphenylethane-1,2-dione, and the coinitiator is an amine.

6. The aqueous dental composition according to claim 1, wherein the stabilizer of formula (I) or (II) is a compound of the following formulae:

(DTBHQ)    (DTBMP)

(DTBBQ)

7. The aqueous dental composition according to claim 1, which contains the stabilizer in an amount from 0.001 to 3 percent by weight based on the total weight of the aqueous dental composition.

8. The aqueous dental composition according to claim 1, which contains the polymerization initiator system in an amount from 0.01 to 10 percent by weight based on the total weight of the aqueous dental composition.

9. The aqueous dental composition according to claim 1, further comprising one or more polymerizable compounds having an acidic group selected from a carboxylic acid group, sulfonic acid ester group, phosphonic acid ester groups and phosphoric acid ester group.

10. The aqueous dental composition according to claim 1, wherein the aqueous dental composition is a dental adhesive composition.

11. The aqueous dental composition according to claim 1, wherein the aqueous dental composition has a color stability as determined according to ISO 7491:2000(en).

12. A stabilizer of the following formula (I') or (II):

(I')

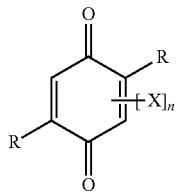 (II)

wherein
the R, which may be the same or different, independently represent a branched $C_{3-8}$ alkyl or alkenyl group, or a $C_{3-8}$ cycloalkyl or cycloalkenyl group,
R' represents a $C_{1-6}$ alkyl or $C_{2-6}$ alkenyl group, or a $C_{1-6}$ fluoroalkyl group or $C_{2-6}$ fluoroalkenyl,
X represents a group selected from a $C_{1-8}$ alkyl group or a $C_{3-8}$ cycloalkyl group, and
n is 0, 1 or 2,
for use in the preparation of an aqueous dental composition having a pH-value of less than 7.

13. The aqueous dental composition according to claim 1, wherein R' represents a $C_{1-6}$ alkyl or $C_{2-6}$ alkenyl group, or a $C_{1-6}$ fluoroalkyl group or $C_{2-6}$ fluoroalkenyl.

14. The aqueous dental composition according to claim 9, wherein the one or more polymerizable compounds having an acidic group includes 10-methacryloyloxydecyl dihydrogen phosphate (MDP) and/or dipentaerythritol pentaacrylate phosphate (PENTA).

* * * * *